(12) United States Patent
Tashiro et al.

(10) Patent No.: US 7,541,195 B2
(45) Date of Patent: Jun. 2, 2009

(54) SUBSTRATE FOR BIOMOLECULE MICROARRAY, BIOMOLECULE MICROARRAY, DEVICE AND METHOD OF PROMOTING INTERACTION, AND METHOD OF DETECTING INTERACTION

(75) Inventors: Hideo Tashiro, Wako (JP); Yasumitsu Kondoh, Wako (JP); Tokuji Kitsunai, Wako (JP); Satoru Hatakeyama, Wako (JP)

(73) Assignee: Riken, Wako-Shi (JP)

( * ) Notice: Subject to any disclaimer, the term of this patent is extended or adjusted under 35 U.S.C. 154(b) by 0 days.

(21) Appl. No.: 10/560,584

(22) PCT Filed: Jun. 9, 2004

(86) PCT No.: PCT/JP2004/008413

§ 371 (c)(1),
(2), (4) Date: May 23, 2006

(87) PCT Pub. No.: WO2004/111644

PCT Pub. Date: Dec. 23, 2004

(65) Prior Publication Data

US 2007/0037155 A1   Feb. 15, 2007

(30) Foreign Application Priority Data

Jun. 13, 2003   (JP) .............................. 2003-170051
Nov. 20, 2003   (JP) .............................. 2003-391083

(51) Int. Cl.
*G01N 33/543* (2006.01)
(52) U.S. Cl. ..................................................... 436/518
(58) Field of Classification Search ...................... None
See application file for complete search history.

(56) References Cited

U.S. PATENT DOCUMENTS

| 6,255,677 | B1 | 7/2001 | Caillat et al. | |
| 6,518,022 | B1 | 2/2003 | Sosnowski et al. | |
| 7,195,872 | B2 * | 3/2007 | Agrawal et al. | 435/6 |
| 2003/0148401 | A1 * | 8/2003 | Agrawal et al. | 435/7.9 |
| 2004/0028875 | A1 * | 2/2004 | Van Rijn et al. | 428/98 |

FOREIGN PATENT DOCUMENTS

| JP | 11-127900 A | 5/1999 |
| JP | 2001-046062 A | 2/2001 |
| JP | 2001-194309 A | 7/2001 |
| JP | 2002-191397 A | 7/2002 |
| JP | 2003-21636 A | 1/2003 |
| JP | 2003-057236 A | 2/2003 |
| JP | 2003-514227 A | 4/2003 |
| JP | 2003-156442 A | 5/2003 |
| WO | WO-98/10273 | 3/1998 |
| WO | WO-03/014739 A1 | 2/2003 |
| WO | WO-03/046508 A2 | 6/2003 |

OTHER PUBLICATIONS

"DNA Microarray Practice Manual that will Necessarily Yield Data, Basic Principle, From Chip preparation to Bioinformatics", 1st edition, Yodosha, 2002, pp. 19-21, 35, 106-108.
R. Levicky et al., J. Am. Chem. Soc., vol. 120, No. 38, pp. 9787-9792, 1998.
Tashiro, Hideo: Riken Research Annual Report, [Online] 2003, pp. 155-160, XP002474378 Retrieved from the Internet: http://www.riken.jp/r-world/info/release/pamphlet/annual/2003/pdf03/0020.pdf> *the whole document*.

* cited by examiner

*Primary Examiner*—Ann Y Lam
(74) *Attorney, Agent, or Firm*—Birch, Stewart, Kolasch & Birch, LLP

(57) ABSTRACT

The substrate for biomolecule microarray has one or more spots for immobilizing a biomolecule. The spot for immobilizing a biomolecule protrudes from the surface of the substrate and has a flat surface for spotting on the top thereof, at least the surface of the substrate around the protruding spot part, the lateral surface of the protruding spot part and the flat surface for spotting are comprised of an electrically conductive substance. Alternatively, the spot for immobilizing a biomolecule protrudes from the surface of the substrate and has a flat surface for spotting on the top thereof, the protruding spot parts adjacent each other border through the lateral surface of the protruding spot part, and at least the lateral surface of the protruding spot part and the flat surface for spotting are comprised of an electrically conductive substance. The biomolecule microarray comprises the above substrate and a biomolecule and the biomolecule is immobilized on at least the flat surface for spotting on the substrate. The device of promoting interaction between biomolecules comprises a biomolecule microarray having one or more biomolecule-immobilized spots on a substrate, an electrode provided so as to face the surface having the biomolecule-immobilized spots of the microarray, and a power source for applying an electric field between the microarray and the electrode. The method of promoting interaction between biomolecules employing the above device. The method of detecting interaction between biomolecules. Provided are a substrate having biomolecule immobilization regions of prescribed shape on a biomolecule microarray, and means by which the interaction of biomolecules is rapidly conducted, the interaction of trace quantities of sample is promoted, and the interaction is detected and analyzed rapidly and with high sensitivity.

25 Claims, 13 Drawing Sheets

(a)

(b)

(a)

(b)

Reflected light image

Fluorescence image p.d.=0V 2min.

p.d.=3V 2min.

(a)

(b)

(c)

Target concentration 0.001 μM NFL 0.01 μM Ubiquitin 0.1 μM β-actin

1 μM gapdh psbP (neg.con.)

(a)          (b)          (c)

(b) Ratio of hybridization intensity ($I_e/I_0$)

(a) Hybridization intensity

SEQUENCE LISTING

<160> NUMBER OF SEQ ID NOS: 18

<210> SEQ ID NO 1
<211> LENGTH: 45
<212> TYPE: DNA
<213> ORGANISM: Artificial Sequence
<220> FEATURE:
<223> OTHER INFORMATION: Synthetic oligonucleotide GAPDH

<400> SEQUENCE: 1
tatgacaatg aatacggcta cagcaacagg gtggtggacc tcatg            45

<210> SEQ ID NO 2
<211> LENGTH: 45
<212> TYPE: DNA
<213> ORGANISM: Artificial Sequence
<220> FEATURE:
<223> OTHER INFORMATION: Synthetic oligonucleotide GAPDH

<400> SEQUENCE: 2
tatgacaatg aatacggcta cagcaacagg gtggtggacc tcatg            45

<210> SEQ ID NO 3
<211> LENGTH: 45
<212> TYPE: DNA
<213> ORGANISM: Artificial Sequence
<220> FEATURE:
<223> OTHER INFORMATION: Synthetic oligonucleotide NFL

<400> SEQUENCE: 3
ggccgttctg cttacagtgg cttgcagagc agctcctact tgatg            45

<210> SEQ ID NO 4
<211> LENGTH: 45
<212> TYPE: DNA
<213> ORGANISM: Artificial Sequence
<220> FEATURE:
<223> OTHER INFORMATION: Synthetic oligonucleotide Ubiquitin2e

<400> SEQUENCE: 4
gtaccaacat tgcctcctag cagagaagtg tgtgtgtgag aagcc            45

<210> SEQ ID NO 5
<211> LENGTH: 45
<212> TYPE: DNA
<213> ORGANISM: Artificial Sequence
<220> FEATURE:
<223> OTHER INFORMATION: Synthetic oligonucleotide beta-actin

<400> SEQUENCE: 5
ttttgtcccc ccaacttgat gtatgaaggc tttggtctcc ctggg            45

<210> SEQ ID NO 6
<211> LENGTH: 45
<212> TYPE: DNA
<213> ORGANISM: Artificial Sequence
<220> FEATURE:
<223> OTHER INFORMATION: Synthetic oligonucleotide gapdh

<400> SEQUENCE: 6
gcagtggcaa agtggagatt gttgccatca acgacccctt cattg            45

<210> SEQ ID NO 7
<211> LENGTH: 45

```
<212> TYPE: DNA
<213> ORGANISM: Artificial Sequence
<220> FEATURE:
<223> OTHER INFORMATION: Synthetic oligonucleotide psbP

<400> SEQUENCE: 7
agccaggaaa tttgtcgaga gcgcagccac ttctttcagt gttgc            45

<210> SEQ ID NO 8
<211> LENGTH: 45
<212> TYPE: DNA
<213> ORGANISM: Artificial Sequence
<220> FEATURE:
<223> OTHER INFORMATION: Synthetic oligonucleotide GAPDH

<400> SEQUENCE: 8
gcagtggcaa agtggagatt gttgccatca acgaccccttt cattg            45

<210> SEQ ID NO 9
<211> LENGTH: 45
<212> TYPE: DNA
<213> ORGANISM: Artificial Sequence
<220> FEATURE:
<223> OTHER INFORMATION: Synthetic oligonucleotide beta-actin

<400> SEQUENCE: 9
ttttgtcccc ccaacttgat gtatgaaggc tttggtctcc ctggg            45

<210> SEQ ID NO 10
<211> LENGTH: 45
<212> TYPE: DNA
<213> ORGANISM: Artificial Sequence
<220> FEATURE:
<223> OTHER INFORMATION: Synthetic oligonucleotide NF-L

<400> SEQUENCE: 10
ggccgttctg cttacagtgg cttgcagagc agctcctact tgatg            45

<210> SEQ ID NO 11
<211> LENGTH: 45
<212> TYPE: DNA
<213> ORGANISM: Artificial Sequence
<220> FEATURE:
<223> OTHER INFORMATION: Synthetic oligonucleotide Ubiquitin 2e

<400> SEQUENCE: 11
gtaccaacat tgcctcctag cagagaagtg tgtgtgtgag aagcc            45

<210> SEQ ID NO 12
<211> LENGTH: 45
<212> TYPE: DNA
<213> ORGANISM: Artificial Sequence
<220> FEATURE:
<223> OTHER INFORMATION: Synthetic oligonucleotide hsc70

<400> SEQUENCE: 12
cctatggtgc agctgtccag gcagccattc tatctggaga caagt            45

<210> SEQ ID NO 13
<211> LENGTH: 45
<212> TYPE: DNA
<213> ORGANISM: Artificial Sequence
<220> FEATURE:
<223> OTHER INFORMATION: Synthetic oligonucleotide rpL3

<400> SEQUENCE: 13
```

```
ggtgaggtga ccaatgactt catcatgctc aaaggctgtg tggtg                45

<210> SEQ ID NO 14
<211> LENGTH: 45
<212> TYPE: DNA
<213> ORGANISM: Artificial Sequence
<220> FEATURE:
<223> OTHER INFORMATION: Synthetic oligonucleotide Akt

<400> SEQUENCE: 14
gctggacaag gacgggcaca tcaagataac ggacttcggg ctgtg                45

<210> SEQ ID NO 15
<211> LENGTH: 45
<212> TYPE: DNA
<213> ORGANISM: Artificial Sequence
<220> FEATURE:
<223> OTHER INFORMATION: Synthetic oligonucleotide Transthyretin

<400> SEQUENCE: 15
accatcgcag ccctgctcag cccatactcc tacagcacca cggct                45

<210> SEQ ID NO 16
<211> LENGTH: 45
<212> TYPE: DNA
<213> ORGANISM: Artificial Sequence
<220> FEATURE:
<223> OTHER INFORMATION: Synthetic oligonucleotide rpS5

<400> SEQUENCE: 16
cattgctgtg aaggagaagt atgccaagta cctgccccac agtgc                45

<210> SEQ ID NO 17
<211> LENGTH: 45
<212> TYPE: DNA
<213> ORGANISM: Artificial Sequence
<220> FEATURE:
<223> OTHER INFORMATION: Synthetic oligonucleotide HCN1

<400> SEQUENCE: 17
gtgccacagc gtgtcacctt gttcagacag atgtcctcgg gagcc                45

<210> SEQ ID NO 18
<211> LENGTH: 45
<212> TYPE: DNA
<213> ORGANISM: Artificial Sequence
<220> FEATURE:
<223> OTHER INFORMATION: Synthetic oligonucleotide Lhb1B2

<400> SEQUENCE: 18
actcaagtta tcctcatggg agctgttgaa ggctacagag tcgcc                45
```

SUBSTRATE FOR BIOMOLECULE MICROARRAY, BIOMOLECULE MICROARRAY, DEVICE AND METHOD OF PROMOTING INTERACTION, AND METHOD OF DETECTING INTERACTION

TECHNICAL FIELD

The present invention relates to a substrate for biomolecule microarray permitting the digital analysis and quantification of biomolecule fixation, a biomolecule microarray characterized in that biomolecules are immobilized on the aforementioned substrate, a device of promoting interaction between biomolecules, a method of promoting interaction between biomolecules, and a method of detecting interaction between biomolecules.

TECHNICAL BACKGROUND

For the purpose of the detection of specific nucleic acids (target nucleic acids), such as genetic diagnosis, identification of pathogenic bacteria, and the detection of single nucleotide polymorphisms, the hybridization between probe nucleic acid and target nucleic acid is employed. In recent years, DNA chips and DNA microarrays in which multiple probe nucleic acids are immobilized on a substrate have been put to practical use to detect target nucleic acids.

In the manufacturing of DNA chips and DNA microarrays, DNA must be arrayed in a form of multiple spots and immobilized on a substrate. For example, one method that is employed to immobilize DNA is to bind a thiol to single-stranded DNA and immobilize the thiolated single-stranded DNA on a metal substrate. The immobilized DNA is then subjected to the action with target DNA of a specimen and the presence or absence of hybrids is detected. For example, hybridization can be detected by detecting the fluorescence from each spot of immobilized DNA that have hybridized with target DNA.

Spotting-type DNA microarrays are prepared by placing liquid droplets containing probe DNA on a substrate and drying them. Thus, although they have the advantage of being inexpensive to produce, there is no guarantee that the DNA that is immobilized on the substrate will be uniform. That is, variations in size and shape of the DNA detection spots result in a drawback of spotting-type DNA microarrays. This drawback arises from, for example, the entire surface of a substrate being treated to immobilize DNA (PLL treatment) or the substrate surface being flat.

Further, in spotting-type DNA microarrays, the presence of solid-phase-forming agents adhering around the DNA detection spots is problematic in that it causes the target DNA to nonspecifically adsorb to the substrate, increasing noise and lowering the S/N ratio.

Further, in fluorescence measurements, an operation referred to as gridding is conducted to identify fluorescent components. In gridding, the number of rows and columns of spots on the array, the spot spacing, and the size of the spot diameter are inputted, and the spots are enclosed in circles (see "DNA Microarray Practice Manual that Will Necessarily Yield Data, Basic Principle, From Chip preparation to Bioinformatics", 1$^{st}$ ed., Yodosha, Dec. 1, 2002, p. 19-21, 35, 106-108). However, when the stamp shape and position are inconstant, the gridding operation requires an extended time during fluorescence analysis and accurate analysis becomes difficult. Further, in gridding, spots cannot be accurately enclosed when the spot positions have shifted. Thus, software is imparted with an automatic position-correcting function. However, all operations are not automated; it is necessary to manually set the spot starting point and visually confirm and correct the grids of all the spots. This operation is extremely complicated. When the DNA spots amount to several thousands, the operation consumes time, thereby analysis speed.

Additionally, hybridization of sample target DNA to probe DNA immobilized on a substrate commonly requires well over ten hours. A large quantity of sample target DNA is also required. Thus, a large amount of time, expense, and effort are required for hybridization and the preparation of a large quantity of sample. In particular, an extremely large amount of target sample is required when analyzing low-expression genes.

Accordingly, it is one object of the present invention to provide a substrate having biomolecule immobilization regions of prescribed shape on a biomolecule microarray, and means by which the interaction of biomolecules, particularly the hybridization of nucleic acids, is rapidly conducted, the interaction of trace quantities of sample is promoted, and the interaction is detected and analyzed rapidly and with high sensitivity.

It is a further object of the present invention to provide a method and device of promoting interaction, by which interaction between biomolecules capable of interaction each other is promoted and efficiently formed.

A still further object of the present invention is to provide means for automatically conducting the gridding operation to permit automation of the collection of fluorescence data from a biomolecule microarray and automation of the digital analysis thereof.

More specifically, the present invention has for its objects to provide a substrate for biomolecule microarray permitting the detection of interaction between biomolecules with high sensitivity and permitting automated gridding, and to provide a biomolecule microarray in which biomolecules are immobilized on such a substrate.

A still further object of the present invention is to provide a method of detecting interaction between biomolecules permitting automated gridding.

DISCLOSURE OF THE INVENTION

Means for achieving the aforementioned objects of the present invention are as follows;
(1) A substrate for biomolecule microarray having one or more spots for immobilizing a biomolecule, characterized in that
said spot for immobilizing a biomolecule protrudes from the surface of the substrate and has a flat surface for spotting on the top thereof, which spot is hereinafter referred to as "protruding spot part"; and
at least the surface of the substrate around the protruding spot part, the lateral surface of the protruding spot part and the flat surface for spotting are comprised of an electrically conductive substance.
(2) The substrate according to (1), wherein said surface of the substrate around the protruding spot part forms a roughly V-shaped bottom surface.
(3) A substrate for biomolecule microarray having one or more spots for immobilizing a biomolecule, characterized in that
said spot for immobilizing a biomolecule protrudes from the surface of the substrate and has a flat surface for spotting on the top thereof, which spot is hereinafter referred to as "protruding spot part";
the protruding spot parts adjacent each other border through the lateral surface of the protruding spot part; and at least said lateral surface of the protruding spot part and the flat surface for spotting are comprised of an electrically conductive substance.

(4) The substrate according to any of (1) to (3), wherein said electrically conductive substance is gold, nickel, platinum, silver, titanium, aluminum, stainless steel, copper, electrically conductive oxide, or electrically conductive plastic.

(5) The substrate according to any of (1) to (4), wherein the entire substrate is comprised of an electrically conductive substance, or the substrate has a coated layer of an electrically conductive substance on the surface thereof.

(6) The substrate according to (5), wherein the substrate having a coated layer of an electrically conductive substance is comprised of glass, metal, silicon or plastic.

(7) The substrate according to any of (1) to (6), wherein said protruding spot part has a height ranging from 10 to 500 μm.

(8) The substrate according to any of (1) to (7), wherein the angle formed between the flat surface for spotting on the top of said protruding spot part and the lateral surface of said protruding spot part is equal to or greater than 90°.

(9) The substrate according to any of (1) to (8), wherein said flat surface for spotting is a roughened surface.

(10) A biomolecule microarray characterized by comprising the substrate according to any of (1) to (9) and a biomolecule; and in that the biomolecule is immobilized on at least the flat surface for spotting on said substrate.

(11) The biomolecule microarray according to (10), wherein said biomolecule is at least one selected from the group consisting of DNA, RNA, PNA, protein, polypeptide, sugar compound, lipid, natural small molecule, and synthetic small molecule.

(12) A device of promoting interaction between biomolecules comprising:
a biomolecule microarray having one or more biomolecule-immobilized spots on a substrate;
an electrode provided so as to face the surface having the biomolecule-immobilized spots of said microarray; and
a power source for applying an electric field between said microarray and said electrode;
characterized in that
the substrate included in said biomolecule microarray has spots for immobilizing biomolecules protruding from the surface of the substrate and having a flat surface for spotting on the top thereof, which spots are hereinafter referred to as "protruding spot parts";
at least said protruding spot part has a surface of an electrically conductive substance;
the biomolecule-immobilized spots are formed by immobilizing biomolecules on the surface of an electrically conductive substance of the flat surface for spotting; and
said substrate has a terminal capable of passing an electric current to said surface of an electrically conductive substance of said protruding spot parts on the surface of said substrate in areas other than the protruding spot parts.

(13) The device according to (12), wherein the surface of said substrate in areas other than the protruding spot parts has a coated layer of an electrically conductive substance, said terminal is comprised in said coated layer of an electrically conductive substance or capable of passing an electric current to said coated layer of an electrically conductive substance, and the coated layer of an electrically conductive substance and the surface of an electrically conductive substance of the protruding spot part are provided as an integrated coated layer of an electrically conductive substance.

(14) The device according to (12) or (13), wherein said biomolecule microarray is the biomolecule microarray according to claim 10 or 11.

(15) The device according to any of (12) to (14), wherein the distance between said flat surface for spotting and the electrode ranges from 1 to 500 μm.

(16) The device according to any of (12) to (15), which comprises a nonelectrically conductive spacer between said microarray and the electrode.

(17) The device according to any of (12) to (16), wherein said electrode provided so as to face the surface having the biomolecule spots of the microarray is a transparent electrode.

(18) The device according to any of (12) to (17), which further comprises a temperature control means.

(19) A method of promoting interaction between biomolecules using the device according to any of (12) to (18), characterized by;
placing a solution comprising a target biomolecule between said microarray and said electrode, and
applying an electric field between said microarray and said electrode.

(20) The method according to (19), wherein said electric field applied between said microarray and said electrode ranges from 0.001 to 10 MV/m.

(21) The method according to (19) or (20), wherein said target biomolecule is labeled with a fluorochrome.

(22) The method according to any of (19) to (21), wherein said solution comprising a target biomolecule comprises at least one buffer substance selected from the group consisting of phenylalanine, histidine, carnosine and arginine.

(23) A method of detecting interaction between biomolecules, characterized in that a confocal detector is used to detect the interaction between a target biomolecule and a biomolecule on each biomolecule-immobilized spot of the microarray according to (10) or (11), that either lies in an environment permitting interaction with the target biomolecule, or has previously lain in an environment permitting interaction with the target biomolecule.

(24) The method according to (23), wherein said microarray either lies in an environment permitting interaction with the target biomolecule, or has previously lain in an environment permitting interaction with the target biomolecule using the method according to any of (19) to (22).

(25) The method according to (23) or (24), wherein said biomolecule on the biomolecule-immobilized spot and/or said target biomolecule are labeled with a fluorochrome.

(26) The method according to any of (23) to (25), wherein, with said confocal detector, said protruding spot parts on the microarray are detected as a reflected image from the difference in intensity of reflected light based on differences in the height and/or shape of the protruding spot parts and other portions on the surface of the microarray.

(27) The method of detecting according to (26), wherein the interaction between biomolecules is detected by detecting fluorescence from said protruding spot parts detected as a reflected image.

(28) A method of making interaction between an immobilized biomolecule and a target biomolecule by contacting a biomolecule microarray having one or more spots immobilized said biomolecule on a substrate surface with a solution comprising said target biomolecule, wherein
said interaction is promoted by adding phenylalanine to said solution comprising a target biomolecule and applying an electric field to said solution so that the target biomolecule comprised in the solution migrates toward said biomolecule-immobilized spot.

(29) The method according to (28), wherein said microarray is one having an electrode, on the surface of which the biomolecule-immobilized spot is provided, on a substrate; an electrode facing said electrode on the substrate is employed; and said electric field is applied between said electrodes in a state where said solution comprising said target biomolecule contacts with said two electrodes.

(30) A method of making interaction between an immobilized biomolecule and a target biomolecule by contacting a microarray having one or more spots immobilized said biomolecule on a substrate surface with a solution comprising said target biomolecule, wherein said solution comprising a target biomolecule comprises at least one buffer substance selected from the group consisting of phenylalanine, histidine, carnosine and arginine, said substrate is one provided with at least a pair of electrodes on the same surface as the surface on which biomolecule-immobilized spots are provided so that the biomolecule-immobilized spots place between said pair of electrodes; and said interaction is promoted by applying an electric field between said electrodes in a state where said solution comprising a target biomolecule contacts with said pair of electrodes

BRIEF DESCRIPTION OF THE DRAWINGS

FIGS.10 b) and 10c ) show fluorescent images obtained in Example 3. In FIG. 10 b) p.d.=0V 2 min. In FIG. 10 c) p.d.=3V 2 min.

BEST MODE FOR CARRYING OUT THE INVENTION

The present invention will be described in greater detail below.

[Substrate]

The substrate for biomolecule microarray of the present invention has one or more spots for immobilizing a biomolecule, and the spot for immobilizing a biomolecule protrudes from the surface of the substrate and has a flat surface for spotting on the top thereof, which spot is hereinafter referred to as "protruding spot part". On the substrate for biomolecule microarray of the present invention, at least the surface of the substrate around the protruding spot part, the lateral surface of the protruding spot part and the flat surface for spotting are comprised of an electrically conductive substance (referred to as "first aspect", hereinafter); or the protruding spot parts adjacent each other border through the lateral surface of the protruding spot part, and at least the lateral surface of the protruding spot part and the flat surface for spotting are comprised of an electrically conductive substance (referred to as "second aspect", hereinafter).

On the substrate of the present invention, the spot for immobilizing a biomolecule is provided on the flat surface on the top of the protruding spot part. Thus, on the substrate of the first aspect of the present invention, the flat surface for spotting (spot for immobilizing a biomolecule) on the top of the protruding spot part is at a one step higher position than the substrate surface around the protruding spot part, there being a difference of height between them.

Figure 1:
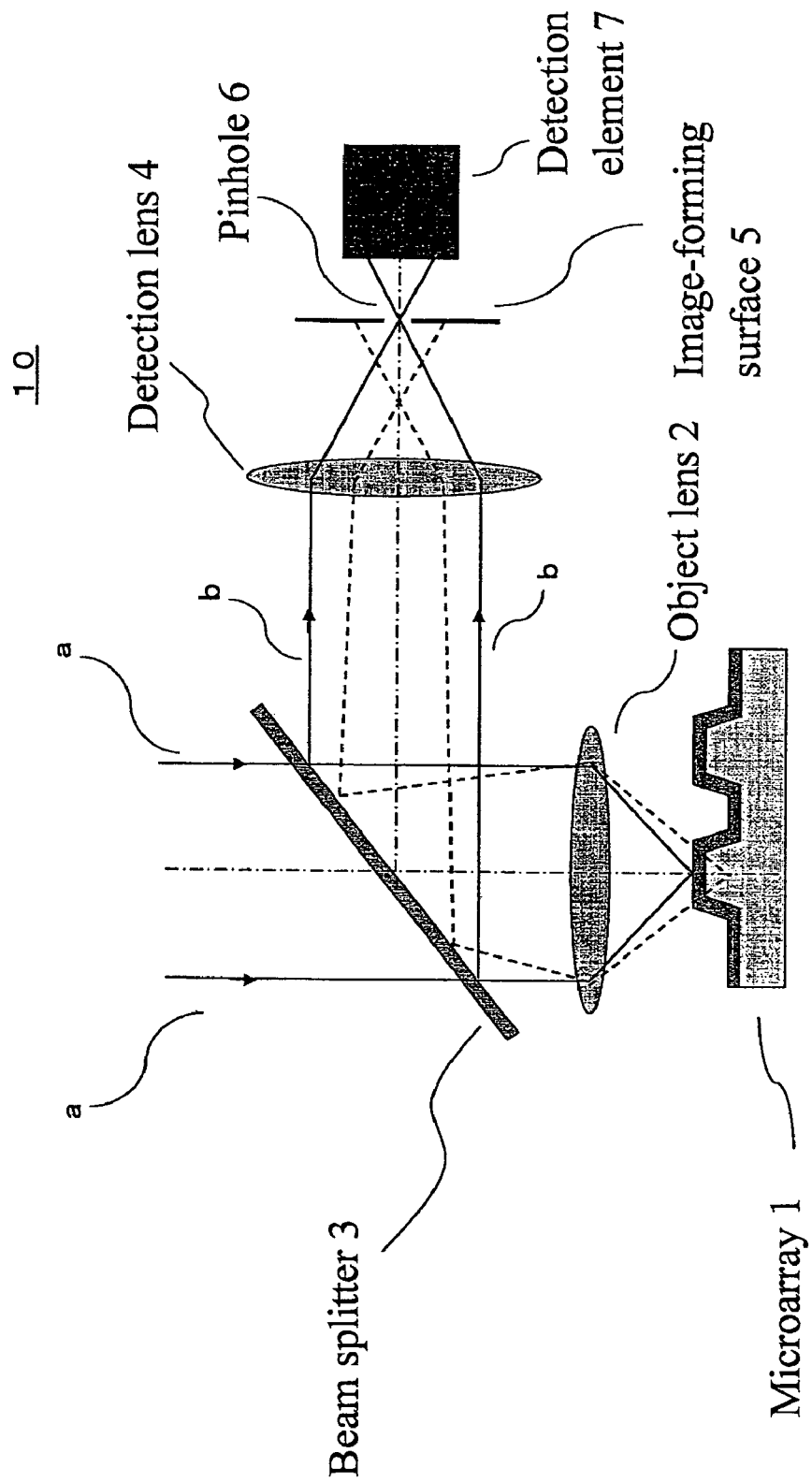
FIG. 1 is a schematic diagram of the optical system of the confocal detector employed in the present invention.

Additionally, a confocal detector employed to detect interaction between biomolecules in the present invention detects fluorescence and reflected light from the focal surface on the sample through pinholes formed in the image-forming surface of an optical system. FIG. 1 shows a schematic diagram of the optical system of the confocal detector 10 employed in the present invention. In FIG. 1, solid line a denotes incident light. Solid line b denotes reflected light or fluorescence from the focal surface. The broken line denotes fluorescence or reflected light from the nonfocal surface. In confocal detector 10, light reflected from the focal surface on microarray 1 and fluorescence released from the focal surface on the sample pass through an object lens 2 and enter a beam splitter 3. Beam splitter 3 corrects the optical path so that the light enters detection lens 4 perpendicularly. The light passes through detection lens 4 and strikes image-forming surface 5. Confocal detector 10 is designed so that the focal point on the sample is also the focal point on the image-forming surface. Thus, light from the focal surface on the sample comes into focus on image-forming surface 5, passes through pinhole 6, and is detected by detection element 7. Additionally, since light from the nonfocal surface on the sample does not come into focus on image-forming surface 5, most of the light does not pass through pinhole 6 and is not detected by detection element 7. In this manner, light from the focal surface can be selectively detected by a confocal detector.

On the substrate of the first aspect of the present invention, when the difference in height between the substrate surface around the protruding spot parts and the flat surface on the top of the protruding spot parts (spots for immobilizing a biomolecule) is greater than the focal depth of the confocal detector employed to detect interaction between biomolecules and target biomolecules, the focal point of the confocal detector can be adjusted to the height of the flat surface on the top of the protruding spot part so that fluorescence and reflected light from the flat surface on the top of the protruding spot part will be detected at higher intensity than fluorescence and light reflected from the substrate surface around the protruding part. Accordingly, in the microarray in which biomolecules are immobilized on the flat surface on the top of a protruding spot part on the substrate of the present invention, information on the spots such as the presence or absence of interaction with a target biomolecule can be detected with high sensitivity.

Figure 5:
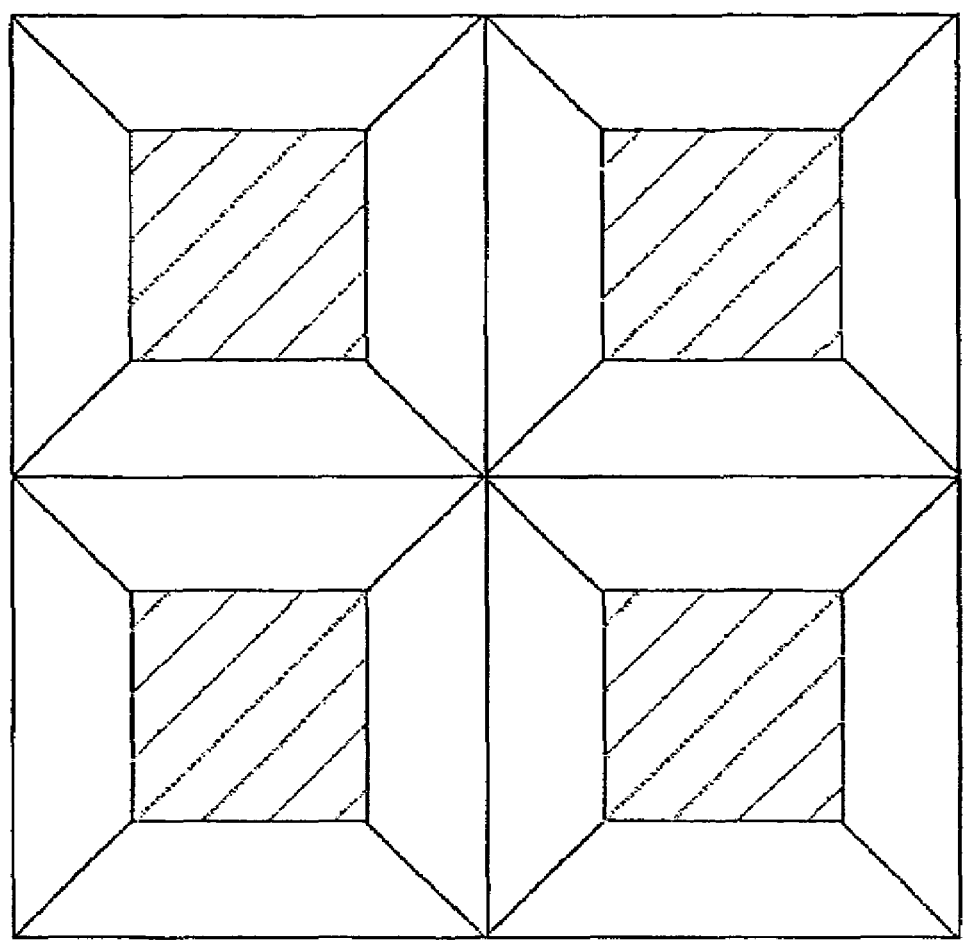
FIG. 5 shows an example of a substrate of the second aspect of the present invention.
Figure 5:
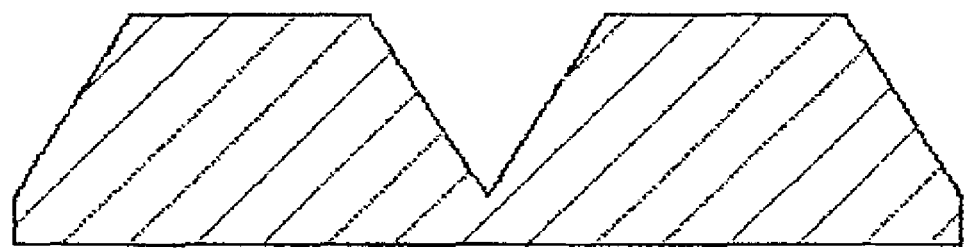

The substrate of the second aspect of the present invention is characterized in that the protruding spot parts adjacent each other border through the lateral surface of the protruding spot part, and at least said lateral surface of the protruding spot part and the flat surface for spotting are comprised of an electrically conductive substance. FIG. 5 shows an example of the substrate of the second aspect of the present invention.

Figure 2:
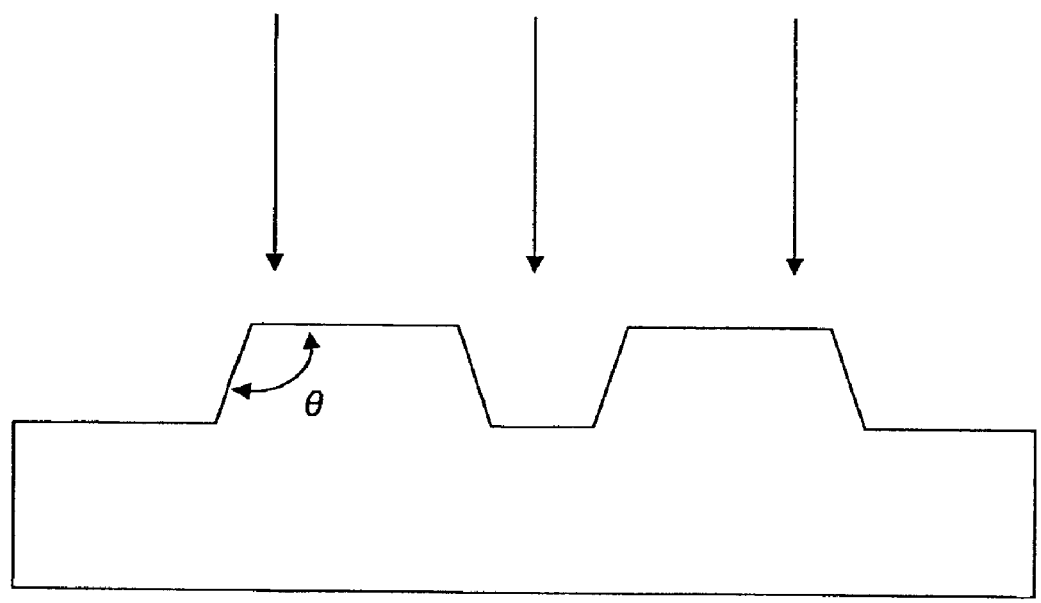
FIG. 2 is a schematic diagram of protruding spot parts on the substrate of the present invention.
Figure 2:
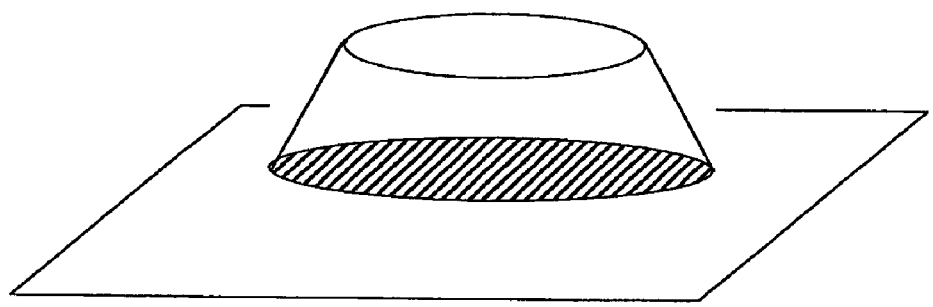

On the substrates of the first and second aspects of the present invention, the angle formed between the flat surface for spotting on the top of the protruding spot part and the lateral surface of the protruding spot part is preferably greater than or equal to 90°, more preferably 90° to 135°. FIG. 2(a) is a cross-sectional view of a portion of the substrate of the present invention. Here, the phrase, "the angle formed between the flat surface for spotting on the top of the protruding spot part and the lateral surface of the protruding spot part" refers to angle θ in FIG. 2(a). For example, the angle θ can be measured from the cross section obtained by cutting the protruding spot part perpendicularly with respect to the substrate surface around the protruding spot.

In this manner, on the substrate of the present invention, having the angle formed between the flat surface for spotting on the top of the protruding spot part and the lateral surface of the protruding spot part be greater than or equal to 90°, that is, having the size of the bottom surface of the protruding spot part be greater than the size of the flat surface on the top of the protruding spot part, is advantageous in that it permits specification of the position and size of the spot for immobilizing a biomolecule. This point will be described in detail below.

As shown in FIG. 2(a), in the course of detecting reflected light using a confocal detector, light reflected from the lateral surface of a protruding spot part, corresponding to light irradiated from a direction perpendicular to the flat surface on the top of the protruding spot part (the light indicated by the arrow in FIG. 2(a)), does not reflect in the same direction as incident light when the angle formed between the flat surface for spotting on the top of the protruding spot part and the lateral surface of the protruding spot part is greater than or equal to 90°. In contrast, light reflected from the flat surface for spotting on the top of a protruding spot part reflects in the same direction as incident light. Thus, in a confocal detector, only light reflected from the flat surface for spotting on the top of a protruding spot part is detected; light reflected from the lateral surface is not detected. In the reflected image thus obtained, the image corresponding to the flat surface for spotting on the top of the protruding spot part is obtained as a reflected image. Most of portions corresponding to the lateral surface of the protruding spot part are not detected in a reflected image, and thus appear as a black fringe. In the reflected image, the interior of the black fringe corresponds to the biomolecule spot. Thus, this reflected image can be used to specify the size and position of the spot. In the present invention, based on this principle, it is possible to automate gridding.

On the substrate of the first aspect of the present invention, when the height of the protruding spot part is greater than or equal to the focal depth of the confocal detector employed to detect interaction, the focal point of the confocal detector can be adjusted to the height of the flat surface for spotting on the top of the protruding spot part. Thus, since light reflected from the substrate surface around the protruding spot part has a different focal point, it is only detected at an intensity much weaker than that of light reflected from the flat surface for spotting on the top of the protruding spot part. In the present invention, this height difference can be exploited to conduct automated gridding. However, even when the height of the protruding spot part is less than the focal depth of the confocal detector used to detect interaction, as stated above, when the portion corresponding to the lateral surface of the protruding spot part appears as a black fringe in a reflected image, it is possible to specify the size and position of the spot.

Further, on the substrate of the first aspect of the present invention, even when the angle formed between the flat surface for spotting on the top of the protruding spot part and the lateral surface of the protruding spot part is less than 90°, when the height of the protruding spot part is greater than or equal to the focal depth of the confocal detector employed to detect interaction, the difference in height between the flat surface for spotting and the substrate surface around the protruding spot part can be exploited to specify the position and size of the flat surface for spotting based on reflected light, and automated gridding can be conducted. When the angle formed between the flat surface for spotting on the top of the protruding spot part and the lateral surface of the protruding spot part is 90°, the protruding spot part can be in the shape of a cylindrical column or a square rod.

Figure 4:
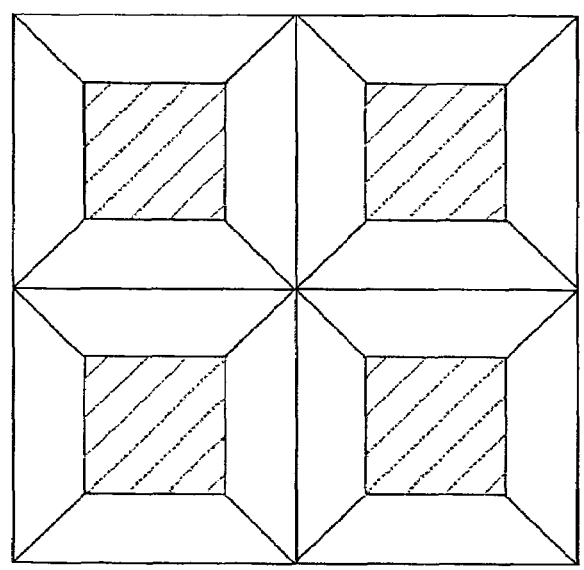
FIG. 4 shows a partially enlarged view of a substrate having a roughly V-shaped bottom surface.
Figure 4:
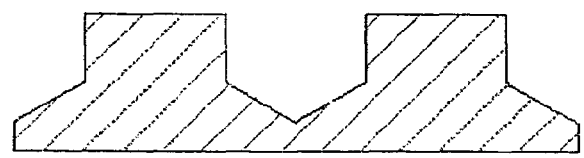

Further, on the substrate of the first aspect of the present invention, the angle formed between the flat surface for spotting on the top of the protruding spot part and the lateral surface of the protruding spot part can be greater than or equal to 90° and the substrate surface around the protruding spot part can form a roughly V-shaped bottom surface. On such a substrate, the intensity of light reflected from the flat surface for spotting that is detected by the confocal detector is greater than the intensity of light reflected from portions other than the flat surface for spotting on the substrate. Thus, this difference in the intensity of reflected light can be used to specify the position and size of the flat surface for spotting. FIG. 4 is a partially enlarged view of a substrate having a "roughly V-shaped bottom surface." In the present invention, the phrase "roughly V-shaped bottom surface" means that the substrate surface around a protruding spot part between adjacent protruding spot parts is not flat, but as shown in FIG. 4, is roughly V-shaped.

The substrate of the first aspect of the present invention is characterized in that at least the surface of the substrate around the protruding spot part, the lateral surface of the protruding spot part, and the flat surface for spotting are comprised of an electrically conductive substance. In view of the ease and cost of manufacturing, in the substrate of the first aspect of the present invention, the substrate surface other than around the protruding spot parts is also desirably comprised of an electrically conductive substance. Further, the substrate of the second aspect of the present invention is characterized in that at least the lateral surface of the protruding spot part and the flat surface for spotting are comprised of an electrically conductive substance.

In the present invention as set forth above, in the substrate of the first aspect, at least the surface of the substrate around the protruding spot part, the lateral surface of the protruding spot part, and the flat surface for spotting, and in the substrate of the second aspect, at least the lateral surface of the protruding spot part and the flat surface for spotting, are comprised of an electrically conductive substance. Thus, as will be described further below, an electrode is provided opposite the substrate and an electric field is applied to promote interaction between a biomolecule immobilized on the flat surface for spotting and a target biomolecule. For example, it is possible to achieve good interaction results even when the concentration of the target biomolecule is low. Further, when the concentrations are identical, it is possible to achieve a prescribed interaction result in a short period.

Further, in the present invention, when the above electrically conductive substance reflects light, the reflected light can be used to specify the size and position of biomolecule-immobilized spots to conduct automated gridding. This point will be described further below.

In the present invention, the height of the protruding spot part can be suitably set to be identical to or greater than the focal depth of the confocal detector employed to detect interaction. In view of the focal depth of the usual confocal detector, the height of the protruding spot part can be from 10 to 500 µm, for example. However, as set forth above, when conducting automated gridding based on detection of the difference in intensity of reflected light based on the difference in shape between the flat surface on the top of the protruding spot part and other portions on the substrate, automated gridding can be conducted even when the height of the protruding spot part is smaller than the focal depth of the confocal detector employed to detect interaction. This point will be described further below.

Further, in the course of setting the height of the protruding spot part, it is also necessary to consider the diameter of the needle employed to form spots of biomolecules (stamping) and the spotting amount of the solution of a biomolecule such as probe nucleic acid. For example, when employing a needle with a diameter of about 130 µm to spot biomolecules on the round protruding spot parts 100 µm in diameter, a protruding spot part having a height of greater than or equal to 15 µm is desirable because surface tension prevents the biomolecule solution from flowing out of the flat surface for spotting on the top of the protruding spot part and thus biomolecules are immobilized only on the spots for immobilizing.

On the substrate of the present invention, the shape of the flat surface for spotting on the top of the protruding spot part can be any shape so long as the biomolecules spotted can be held. For example, the shape may be round or square. The size of the above flat surface for spotting can be suitably set based on the needle employed in spotting and the amount of biomolecule solution that is spotted. For example, it can be 10 to 500 µm. Here, the phrase "size of the flat surface for spotting" refers to the diameter when, for example, the flat surface for spotting is round in shape, and to the length of a side when the flat surface for spotting is square in shape.

The shape of the bottom surface of the protruding spot part is not specifically limited. In consideration of the ease of manufacture, this shape is desirably identical to the shape of the flat surface for spotting. FIG. 2(b) is a schematic diagram of a protruding spot part on the substrate of the present invention. Here, the phrase, "the shape of the bottom surface of the protruding spot part" refers to the hatched portion in FIG. 2(b).

Figure 3:
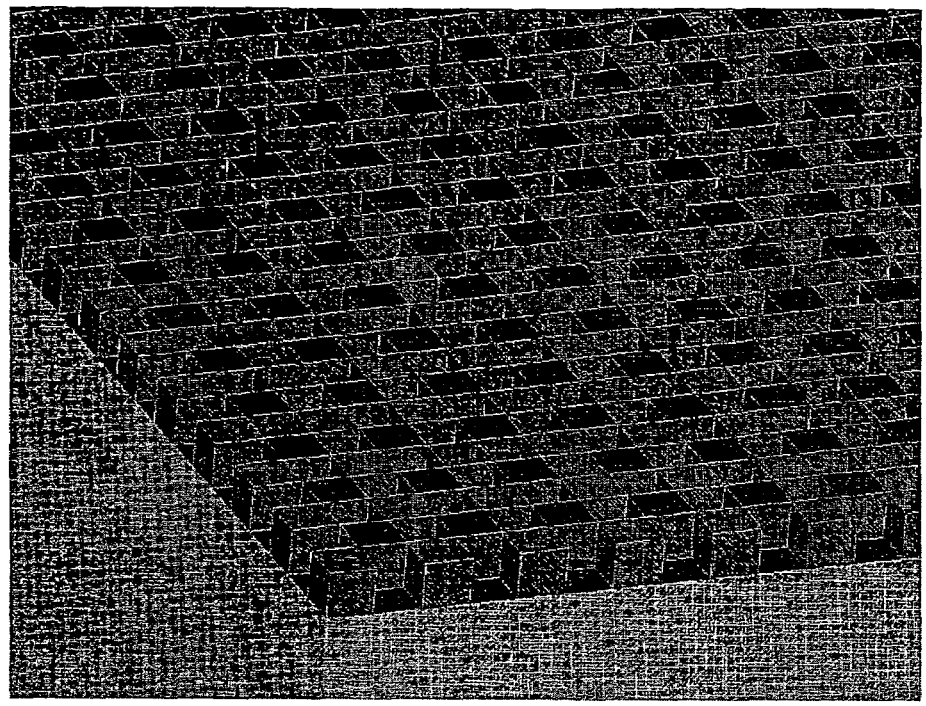
FIG. 3 shows an example (partially enlarged view) of a flat surface for spotting, that is a roughened surface, on the substrate of the present invention.

The flat surface for spotting on the top of the protruding spot part can be a roughened surface. For example, on the flat surface for spotting on the top of the protruding spot part, there may be irregularities with a depth within the focal depth of the confocal detector employed to detect interaction in a roughly horizontal direction to a depth direction. FIG. 3 shows an example (partially enlarged view) of a roughened flat surface for spotting. The flat surface for spotting provided with a lattice-like shape with squares of several micrometers, as shown in FIG. 3, is an example of a roughened flat surface for spotting. By roughening the flat surface for spotting in this manner, as described further below, a strong electric field is generated at the edges of the irregularities when concentrating the target biomolecule by electrophoresis or dielectrophoresis, affording the advantage of further promoting interaction.

The method of roughening the flat surface for spotting is not specifically limited. For example, when the substrate of the present invention is a molded plastic substrate, a substrate with roughened flat surfaces for spotting can be prepared using a finely processed mold obtained by reverse transferring, with electroforming, a base material that has been etched by photolithography.

The entire substrate of the present invention can be comprised of an electrically conductive substance, or the substrate of the present invention can have a coated layer of an electrically conductive substance on the surface thereof.

As set forth above, when conducting automated gridding based on a reflected image, the electrically conductive substance is selected from among substances having light-reflecting properties.

Further, when a probe nucleic acid is immobilized using the bond of metal and a thiol group, the electrically conductive substance is selected from among metals having the ability to bind with thiol groups.

Examples of the electrically conductive substance are metals (such as gold, nickel, platinum, silver, titanium, aluminum, stainless steel, and copper), electrically conductive oxides (such as $In_2O_5/SnO_2$), and electrically conductive plastics (such as polyacetylene).

Examples of the substrate having a coated layer of an electrically conductive substance are glass, silicon, and plastic substrates—specifically, polypropylene substrates—the surfaces of which have been coated with the above-described electrically conductive substances. The thickness of the coated layer of an electrically conductive substance on the substrate is not specifically limited, and can be 0.1 to 10 µm, for example.

In the present invention, when the substrate is comprised of metal, the substrate of the present invention can be cast by pouring molten metal into a casting mold having indentations corresponding to protruding spot parts of desired shape. A metal substrate can also be obtained by press molding. The substrate of the present invention can also be in the form of a metal substrate coated with an electrically conductive substance.

When the substrate of the present invention has a coating of an electrically conductive substance on a substrate made of silicon or plastic, for example, the substrate of the present invention can be obtained by molding silicon or plastic with a pressing mold having indentations corresponding to protruding spot parts of desired shape and coating the substrate made of silicon or plastic with an electrically conductive substance by vapor deposition, plating, or the like.

The substrate of the present invention can also be manufactured by applying an electrically conductive coated layer to a flat substrate and then forming protruding spot parts by etching or the like.

An example of a method of manufacturing the substrate of the present invention when it comprises a gold coated layer on a glass substrate will be described below. However, the present invention is not limited to this form.

First, a vacuum vapor deposition device is used to vapor-deposit chromium, titanium, nickel, or the like on the surface of a glass slide. Next, gold is vapor-deposited thereover. Positive resist is then applied by spin coating to the glass slide that has been vapor-deposited with gold, and the substrate is baked for one hour in an oven at 60° C., for example.

Next, the glass slide is irradiated with ultraviolet radiation through a photomask using a UV exposure device. The photomask employed has a pattern corresponding to protruding spot parts of desired shape. Following UV irradiation, development is conducted with a developing solution to form a resist pattern on the surface of the gold-deposited glass slide.

Next, the gold surface around the resist pattern is etched with a gold etchant. Following etching of gold, the substrate is washed with ultrapure water, again etched with an etchant to remove the chromium, titanium, nickel, or the like deposited under the gold, and washed with ultrapure water.

After dissolving the resist with acetone or the like, the substrate is washed with ultrapure water, immersed in piranha solution (sulfuric acid:hydrogen peroxide=1:1) for 10 minutes, for example, to completely remove any remaining resist, and then washed with ultrapure water. This yields a glass substrate having a gold pattern corresponding to the photomask.

Next, the above substrate is immersed in hydrofluoric acid to etch the exposed glass surface. The concentration of the hydrofluoric acid employed and the immersion time can be suitably set based on the desired height of the protruding spot parts.

Next, in the same manner as above, gold, chromium and the like are etched and the substrate is cleaned with piranha solution and ultrapure water, yielding a glass substrate having protruding spot parts of desired shape.

This glass substrate can be vapor-deposited with chromium and then gold in the same manner as above to obtain a substrate having both protrusions and a gold coating.

In the present invention, neither the overall size of the substrate, the number of protruding spot parts on the substrate, nor their degree of integration is limited; these may all be suitably set. For example, the substrate of the present invention may be in the form of a substrate 10 to 20,000 mm$^2$ in size having roughly from 10 to 50,000 protruding spot parts.

[Biomolecule Microarray]

The biomolecule microarray of the present invention is characterized by comprising the substrate of the present invention and a biomolecule; and in that the biomolecule is immobilized on at least the flat surface for spotting on the substrate. The biomolecule can be at least one selected from the group consisting of DNA, RNA, PNA, protein, polypeptide, sugar compound, lipid, natural small molecule, and synthetic small molecule. It can be selected based on the objective.

Examples of the sugar compound are monosaccharides, oligosaccharides, polysaccharides, sugar-chain complexes, glycoproteins, glycolipids, and derivatives thereof.

Examples of the lipid are fatty acids, phospholipids, glycolipids, and glycerides.

Examples of the natural small molecule are hormone molecules, antibiotic substances, poisons, vitamins, physiologically active substances, and secondary metabolites.

Examples of the synthetic small molecule are synthetic products of natural small molecules and derivatives thereof.

In the present invention, when the biomolecule is nucleic acid and the electrically conductive substance is metal, to immobilize the probe nucleic acid to spots for immobilizing a biomolecule (protruding spot parts), a solution containing nucleic acid having on one end a group reactive with the metal of the flat surface for spotting on the top of the protruding spot parts can be employed as a spotting solution. An example of such a group is a thiol group. A nucleic acid chain having a thiol group can be immobilized on a metal surface by known methods. For example, see J. Am. Chem. Soc. 1998, 120, 9787-9792.

The following methods of processing a metal (where a surface oxide coating is activated so as to present hydroxyl groups) may be employed as the method of immobilizing DNA on a metal surface:

(1) Immobilization of DNA on a substrate surface processed with aminosilane by UV irradiation;

(2) Immobilization of biotinylated DNA on a substrate surface that has been sequentially treated with aminosilane, NHS (N-hydroxysuccinimide)-biotin, and avidin.

(3) Immobilization of biotinylated DNA on a substrate surface that has been sequentially treated with aminosilane, maleimide-biotin, and avidin.

(4) Immobilization of aminated DNA on a substrate surface that has been treated with aminosilane followed by glutaldehyde.

(5) Immobilization of aminated DNA on a substrate surface that has been treated with aminosilane followed by carbodiimide.

(6) Immobilization of carboxylated DNA on a substrate surface that has been treated with aminosilane.

(7) Immobilization of phosphorylated DNA on a substrate surface that has been treated with aminosilane.

(8) Immobilization of thiolated DNA on a substrate surface that has been treated with aminosilane followed by an NHS-maleimide compound.

(9) Immobilization of aminated DNA on a substrate surface that has been treated with epoxysilane.

(10) Immobilization of thiolated DNA on a substrate surface that has been treated with thiolsilane.

Biomolecules other than DNA can also be immobilized by UV irradiation or through a functional group such as a thiol group, amino group, carboxyl group, phosphoric acid group, or the like as set forth above.

Spotting of the biomolecule solution on the flat surface for spotting can be conducted by the usual methods. For example, spotting can be conducted by contacting a needle holding the biomolecule solution in its tip with the flat surface for spotting on the top of the protruding spot parts. Examples of the spotting device employed are described in Japanese Unexamined Patent Publication (KOKAI) Nos. 2001-46062 and 2003-57236. The spot amount can be suitably set based on the size of the flat surface for spotting and the height of the protruding spot parts so that the biomolecule solution does not flow out of the flat surface for spotting.

[Device and Method of Promoting Interaction]

The present invention further relates to a device of promoting interaction between biomolecules comprising:

a biomolecule microarray having one or more biomolecule-immobilized spots on a substrate;

an electrode provided so as to face the surface having the biomolecule-immobilized spots of said microarray; and a power source for applying an electric field between said microarray and said electrode;

characterized in that the substrate included in said biomolecule microarray has spots for immobilizing biomolecules protruding from the surface of the substrate and having a flat surface for spotting on the top thereof (protruding spot parts);

at least said protruding spot part has a surface of an electrically conductive substance;

the biomolecule-immobilized spots are formed by immobilizing biomolecules on the surface of an electrically conductive substance of the flat surface for spotting; and said substrate has a terminal capable of passing an electric current to said surface of an electrically conductive substance of said protruding spot parts on the surface of said substrate in areas other than the protruding spot parts.

Examples of the interaction between biomolecules are hybridization of probe nucleic acid and target nucleic acid, antigen-antibody interaction, receptor-ligand interaction, protein-protein interaction, and DNA-protein interaction.

It is preferable that the surface of said substrate in areas other than the protruding spot parts has a coated layer of an electrically conductive substance, said terminal is comprised in said coated layer of an electrically conductive substance or capable of passing an electric current to said coated layer of an electrically conductive substance, and the coated layer of an electrically conductive substance and the surface of an electrically conductive substance of the protruding spot part are provided as an integrated coated layer of an electrically conductive substance. The biomolecule array in the above device can be the above-described biomolecule microarray of the present invention.

The present invention further relates to a method of promoting interaction between biomolecules using the aforementioned device of promoting interaction between biomolecules characterized by;

placing a solution comprising a target biomolecule between said microarray and said electrode, and applying an electric field between said microarray and said electrode.

Since the biomolecule microarray in the device has protruding spot parts, the electric field density increases between the flat surface on the top of the protruding parts on the microarray, on which a biomolecule is immobilized, and the opposing surface of the electrode (opposite electrode) provided so as to face the surface having biomolecule spots of the microarray. The target biomolecules in the solution are concentrated in the vicinity of the protruding parts by electrophoresis (when a direct current power source is employed) or dielectrophoresis (when an alternating power source is employed).

Thus, interaction between biomolecules immobilized on the protruding spot parts and the target biomolecules can be promoted. In particular, when the flat surface for spotting in the above biomolecule microarray, on which the biomolecules are immobilized, is a roughened surface, for example, irregularities having a depth within the focal depth of a confocal detector are provided in a roughly horizontal direction to a depth direction on the flat surface for spotting, such advantages can be obtained that an intense electrical field is produced at the edge of the irregularities and thus the interaction is further promoted.

The above opposite electrode is not specifically limited so long as it be capable of applying an electric field between the biomolecule microarray and the opposite electrode. FIG. 6(a) shows a schematic diagram of the device of promoting interaction between biomolecules of the present invention and FIG. 6(b) shows a cross-sectional view of the same. In the present invention, the opposite electrode can be a substrate comprised of an electrically conductive substance such as metal, electrically conductive oxide, or electrically conductive plastic. Further, it can be a substrate having a coating later of an electrically conductive substance on a surface opposing the microarray. In the present invention, in particular, when the opposite electrode is a transparent electrode of indium tin oxide (ITO) or tin oxide, reflected light and fluorescence can be detected with a confocal detector from above the transparent electrode simultaneously with the interaction between biomolecules, permitting real time detection of the interaction. Further, when the substrate included in the biomolecule microarray is optical-transparent glass or plastic having a transparent electrically conductive coated layer thereover, or when the entire substrate is comprised of a transparent electrically conductive substance, real time detection is similarly possible.

Further, in the device of promoting interaction, the power source for applying an electric field between the biomolecule microarray and the opposite electrode may be either a direct current or alternating current power source. An alternating current power source is preferably employed. When employing a direct current power source and applying a high voltage, there is a risk that the target biomolecule solution will be electrically degraded by the high voltage and that bubbles will appear. Thus, the use of a low voltage is desirable when employing a direct current power source. When employing DNA as the target biomolecule and using a direct current power source, the electric field is desirably applied so that the protruding spot part side is made the positive side, since DNA is negatively charged. When employing an alternating current power source, since electrical degradation of the target biomolecule solution tends to generate bubbles for low-frequency currents, a high-frequency alternating current is desirably employed.

In the device of promoting interaction, a spacer comprised of a nonelectrically conductive material may be inserted between the biomolecule microarray and the opposite electrode in such a manner as not to cover the area in which the protruding spot parts of the biomolecule microarray are present. Examples of such nonelectrically conductive materials are rubber, glass, and plastic. In the device of the present invention, the thickness of the spacer can be used to set the distance between the flat surface for spotting on the biomolecule microarray and the opposite electrode. Further, the space enclosed with the spacer can be filled with a solution containing the target biomolecule. The distance between the flat surface for spotting and the opposite electrode can be suitably set within a range permitting to concentrate of the target biomolecule by electrophoresis or dielectrophoresis; for example, 1 to 500 µm.

The device of promoting interaction desirably further comprises a temperature control means, such as a heater. The interaction can be further promoted by regulating the temperature of the area around the biomolecules in a manner suited to interaction with the temperature control means.

In the device, the electric field that is applied between the biomolecule microarray and the opposite electrode can be suitably set within a range permitting to concentrate of the target biomolecule by electrophoresis or dielectrophoresis while taking into account the distance between the biomolecule microarray and the opposite electrode. For example, it can be set within a range of 0.001 to 10 MV/m. As set forth further below, based on the type of buffer employed in the target biomolecule solution, the electric field applied is suitably set to achieve a high interaction promoting effect.

In the present invention, in order to detect interaction between biomolecules through the detection of fluorescence with a confocal detector, the target biomolecules employed in the above method of promoting interaction are desirably labeled with a fluorochrome. The target biomolecules can be labeled with a fluorochrome by known methods. Further, in the present invention, the biomolecules immobilized on the microarray may be labeled with a fluorochrome. The fluorescent labeling of the biomolecules immobilized on the microarray may also be conducted by known methods.

In the present invention, the target biomolecule solution may contain a buffer. The target biomolecule solution desirably contains a buffer having a dissociation constant (pKa) of around 6 to 8. To efficiently promote hybridization of probe nucleic acid and target nucleic acid, the pH is desirably in the neutral range. Thus, the use of a buffer having a buffering ability in the neutral range is desirable. Specific examples are buffers containing the following buffering substances: phenylalanine, carnosine, arginine, histidine, 2-(N-morpholine)ethanesulfonic acid (MES), maleic acid, 3,3-dimethylglutamic acid, carbonic acid, 4-hydroxymethylimidazol, citric acid, dimethylaminoethylamine, proline acid, glycerol-2-phosphoric acid, piperazine-N,N'-bis(2-ethanesulfonic acid) (PIPES), ethylenediamine, imidazole, 3-(N-morpholine)propanesulfonic acid (MOPS), phosphoric acid, N-tris (hydroxymethyl)methyl-2-aminoethanesulfonic acid (TES), 4-methylimidazol, N-2-hydroxyethylpiperazine-N'-2-ethanesulfonic acid (HEPES), N-ethylmorpholine, triethanolamine, and tris(tris(hydroxymethyl)aminomethane).

When the conductivity of the buffer employed in the target biomolecule solution is excessively high, migration of ions in the buffer may reduce the concentrating effect on the target biomolecules. Accordingly, in the present invention, a buffer with a conductivity of 10 to 500 $\mu\Omega^{-1}/m$ is desirably employed, with the use of a buffer having a conductivity of 10 to 100 $\mu\Omega^{-1}/m$ being preferred. When buffer conductivity falls within the above-stated range, the interaction between biomolecules can be effectively promoted. The concentration of the buffer is desirably adjusted so that the conductivity falls within the above-stated range.

From the above perspectives, specific examples of desirable buffers are those comprising phenylalanine, histidine, carnosine and arginine as a buffer substance. As will be described in Example 5 below, a particularly strong hybridization signal can be obtained when the hybridization of probe nucleic acid and target nucleic acid is conducted with a target biomolecule solution containing phenylalanine, and when an electric field is applied, a hybridization signal can be obtained that is at least twice as intense as that obtained when no electric field is applied. Thus, phenylalanine is a particularly effective buffer substance in the present invention for promoting interaction between biomolecules by applying an electric field.

The electric field that is applied between the microarray and the electrode is desirably set based on the buffer employed so as to yield a strong effect in promoting interaction between biomolecules. For example, the application of an electric field falling within a range of 0.5 to 1.0 MV/m when employing phenylalanine, 0.5 to 1.0 MV/m when employing histidine, 0.25 to 0.75 MV/m when employing carnosine, and 0.1 to 0.3 MV/m when employing arginine as buffer is desirable.

[Method of Detecting Interaction]

The present invention further relates to a method of detecting interaction between biomolecules, characterized in that a confocal detector is used to detect the interaction between a target biomolecule and a biomolecule on each biomolecule-immobilized spot of the microarray of the present invention, that either lies in an environment permitting interaction with the target biomolecule, or has previously lain in an environment permitting interaction with the target biomolecule. The principle of detection of reflected light or fluorescence using a confocal detector is as set forth above. In the method of detecting interaction of the present invention, gridding can be automated by using a confocal detector to specify the spot size and position based on a reflected image using the above principle. That is, based on the present invention, the biomolecule-immobilized spots on the microarray can be detected as a reflected image from the difference in intensity of reflected light based on differences in the height and/or shape of biomolecule-immobilized spots and other portions on the surface of the microarray. Further, a fluorescent image corresponding to the spots can be obtained by selectively detecting the fluorescence of fluorescently labeled biomolecules (biomolecules immobilized on spots and/or target biomolecules) on the flat surfaces for spotting by matching the focal point of the confocal detector to the height of the flat surfaces for spotting on the top of protruding spot parts on the microarray when detecting fluorescence from the microarray with a confocal detector. In the present invention, the reflected image and fluorescent image thus obtained can be superposed to specify spots on which interaction is occurring on the microarray, and based on the fluorescent intensity, measure the degree of interaction. In the present invention, an intercalator can be employed and the interaction can be detected by measuring fluorescence from the intercalator.

Figure 7:
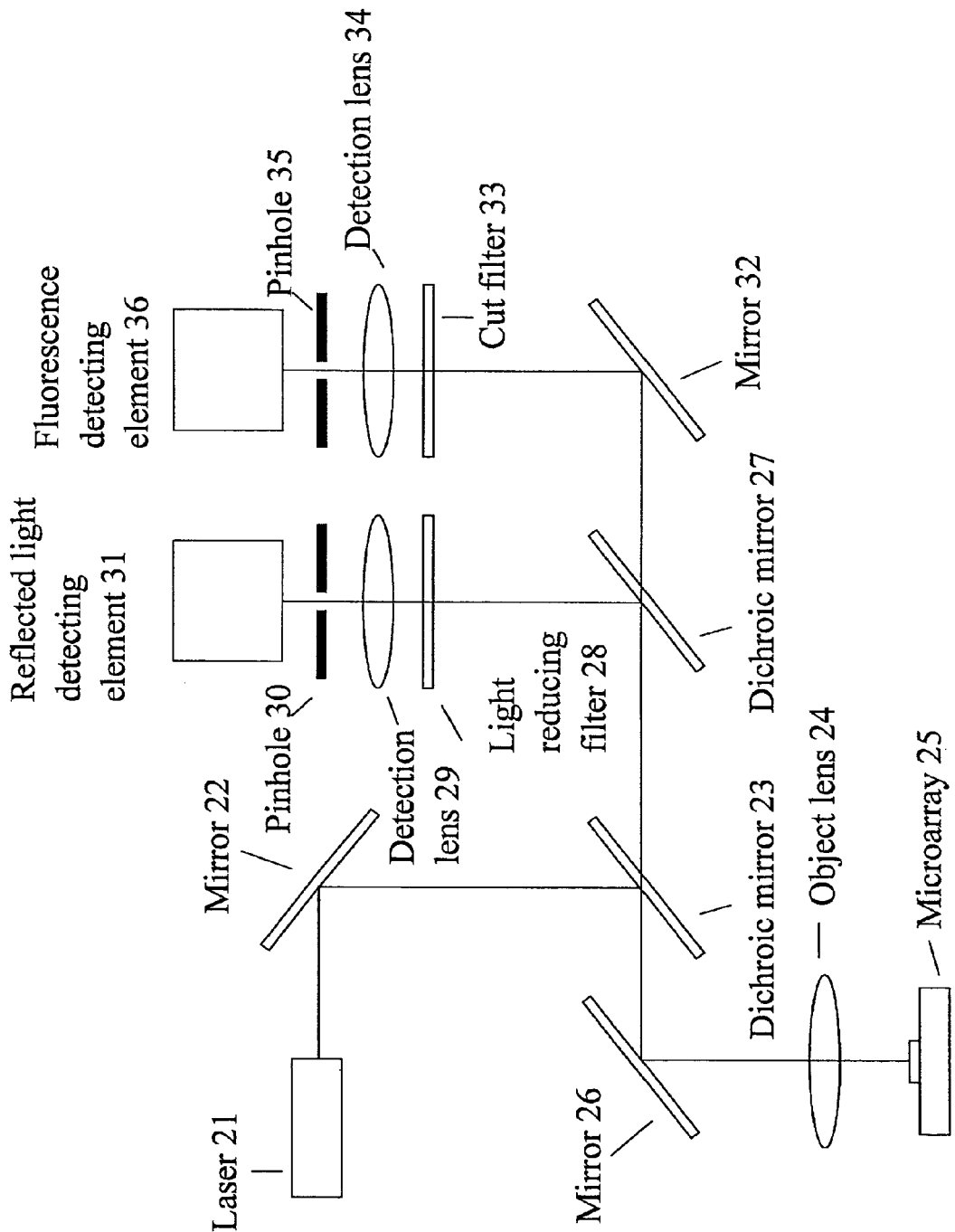
FIG. 7 shows a schematic diagram of the optical system of a confocal scanner capable of simultaneously detecting reflected light and fluorescence.

In the present invention, the use of a confocal scanner capable of simultaneously detecting reflected light and fluorescence is particularly desirable. FIG. 7 shows an example of such a device. In the device shown in FIG. 7, an excitation beam generated by excitation light source (laser) 21 passes through mirror 22, dichroic mirror 23, mirror 26, and object lens 24, where it is directed onto a sample (microarray) 25. The reflected light passes through object lens 24, mirror 26, dichroic mirror 23 (which passes some of the reflected light (not more than several percent)), dichroic mirror 27, light reducing filter 28, detection lens 29, and pin hole 30, where it is directed onto reflected light detecting element 31. The fluorescence passes through two dichroic mirrors 23 and 27, reflects off mirror 32, and passes through cut filter 33, detection lens 34, and pin hole 35, where it is directed onto fluorescence detecting element 36. Based on this device, the biomolecule-immobilized spots on the microarray can be detected as reflected images from the difference in intensity of reflected light based on differences in the height and/or shape of biomolecule-immobilized spots and other portions on the surface of the microarray while simultaneously detecting interaction between biomolecules through the detection of fluorescence from the spots.

The present invention further relates to a method of making interaction between a biomolecule immobilized and a target biomolecule by contacting a biomolecule microarray having one or more spots formed by immobilization of said biomolecule on a substrate surface with a solution comprising said target biomolecule, wherein said interaction is promoted by adding phenylalanine to said solution comprising a target biomolecule and applying an electric field to said solution so that the target biomolecule comprised in the solution migrates toward said biomolecule-immobilized spot.

In the above method, the type of the biomolecule employed, the method of immobilizing the biomolecule on the substrate surface, and the type of interaction between biomolecules are as set forth above. Examples of methods of bringing the biomolecule microarray into contact with the solution comprising a target biomolecule are: immersing the biomolecule microarray in the solution comprising the target biomolecule, and dripping the solution comprising the target biomolecule onto a surface comprising the biomolecule-immobilized spots of the microarray. As is set forth further below, when an electrode is positioned opposite the microarray, the solution comprising the target biomolecule can be brought into contact with the biomolecule microarray by positioning the solution between the microarray and the electrode.

In the above method, an electric field is applied to the solution so that the target biomolecule comprised in the solution comprising the target biomolecule migrates toward the biomolecule-immobilized spots on the substrate. In this case, when the electric field is applied with a direct current power source, the target biomolecule migrates toward the biomolecule-immobilized spots on the substrate by electrophoresis, and when the electric field is applied with an alternating current power source, the target biomolecule migrates toward the biomolecule-immobilized spots on the substrate by dielectrophoresis. In the method of making interaction between biomolecules of the present invention, applying an electric field in this manner to cause the target biomolecule to migrate toward biomolecule spots on the substrate increases the concentration of target biomolecules in the vicinity of the biomolecule spots, promoting interaction between biomolecules. In the present invention, phenylalanine, with its low conductivity and markedly high effect in promoting interaction between biomolecules when an electric field is applied, can be incorporated into the target biomolecule solution to markedly promote interaction between biomolecules.

In the method of making interaction between biomolecules of the present invention, the conductivity of the phenylalanine employed is preferably 10 to 500 $\mu\Omega^{-1}/m$, more preferably 10 to 100 $\mu\Omega^{-1}/m$, as set forth above. The concentration of phenylalanine is desirably suitably adjusted to achieve a conductivity falling within this range.

The biomolecule microarray employed in the method of making interaction between biomolecules can be a biomolecule microarray having an electrode, on the surface of which the biomolecule-immobilized spot is provided, on a substrate. The biomolecule microarray of the present invention can be employed as such a microarray.

When employing a biomolecule microarray having an electrode, on the surface of which the biomolecule-immobilized spot is provided, on a substrate, the interaction between the biomolecule immobilized on the substrate surface and the target biomolecule can be promoted by using an electrode facing the electrode on the substrate and applying the electric field between the above electrodes in a state where the solution comprising the target biomolecule and phenylalanine, which can markedly promote interaction when an electric field is applied, contacts with two electrodes mentioned above to increase the concentration of target biomolecules in the vicinity of the biomolecule-immobilized spots. In this method, the above-described device of promoting interaction between biomolecules of the present invention can be employed, which comprises a microarray having an electrode, on the surface of which the biomolecule-immobilized spot is provided, on a substrate and an electrode facing the electrode on the substrate and in which the biomolecule microarray can be brought into contact with the solution comprising the target biomolecule by placing the solution comprising the target biomolecule between the microarray and the electrode facing the electrode on the substrate. The application of an electric field between the electrodes is as set forth above in the description of the device of promoting interaction between biomolecules of the present invention.

The present invention further relates to a method of making interaction between a biomolecule immobilized and a target biomolecule by contacting a microarray having one or more spots formed by immobilization of said biomolecule on a substrate surface with a solution comprising said target biomolecule, wherein said solution comprising a target biomolecule comprises at least one buffer substance selected from the group consisting of phenylalanine, histidine, carnosine and arginine, said substrate is one provided with at least a pair of electrodes on the same surface as the surface on which biomolecule-immobilized spots are provided so that the biomolecule-immobilized spots place between said pair of electrodes; and said interaction is promoted by applying an electric field between said electrodes in a state where said solution comprising a target biomolecule contacts with said pair of electrodes.

In the above method, the type of biomolecules employed, the method of immobilizing the biomolecules on the substrate surface, and the type of interaction between the biomolecules are as set forth above. Examples of methods of bringing the biomolecule microarray into contact with the solution comprising a target biomolecule are: immersing the biomolecule microarray in the solution comprising the target biomolecule, and dripping the solution comprising the target biomolecule onto a surface comprising the biomolecule-immobilized spots of the microarray.

Figure 14:
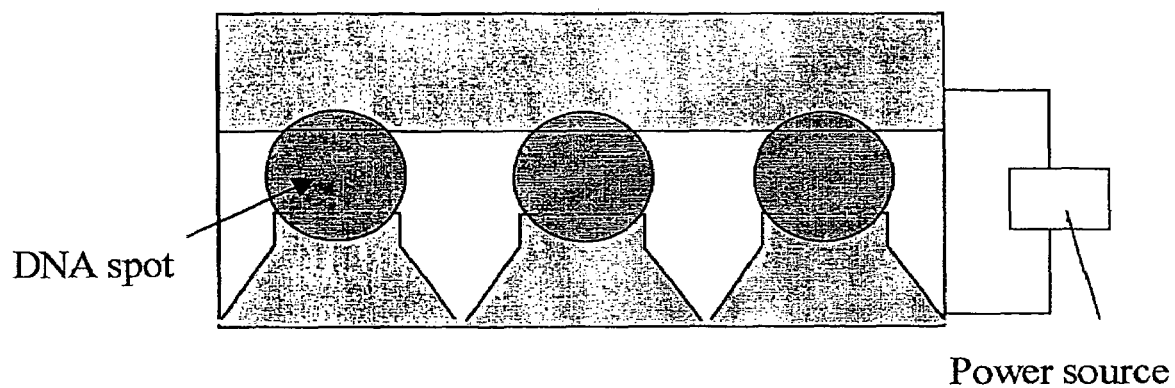
FIG. 14 is an example of a substrate that can be used in the method of making interaction between biomolecules of the present invention.

The substrate employed in the above-mentioned method is one provided with at least a pair of electrodes on the same surface as the surface on which biomolecule-immobilized spots are provided so that the biomolecule-immobilized spots place between a pair of electrodes mentioned above. FIG. 14 shows an example of such a substrate. In the substrate of FIG. 14 for example, a layer comprised of an electrically conductive substance is formed on a part of the substrate by photolithography or the like to form a pair of electrodes opposed each other. In this method, a biomolecule microarray prepared by immobilizing biomolecules on such a substrate can be employed. In this method, such a microarray is employed, a biomolecule microarray having biomolecule-immobilized spots and a solution comprising a target biomolecule are brought into contact between the electrodes, and an electric field is applied between the electrodes in a state where the target biomolecule solution contacts with the electrodes. In this manner, the target biomolecules are caused to migrate toward the biomolecule-immobilized spots by dielectrophoresis (when an alternating current power source is employed) or by electrophoresis (when a direct current power source is employed) to increase the concentration of the target biomolecules in the vicinity of the biomolecule-immobilized spots, thereby promoting interaction between the biomolecules. In particular, in the present invention, interaction between the biomolecules can be markedly promoted by incorporating into the target biomolecule solution at least one buffer substance selected from the group consisting of phenylalanine, histidine, carnosine and arginine, particularly phenylalanine, having the markedly high effect in promoting interaction between biomolecules with the application of an electric field. The electric field that is applied between the electrodes can be suitably set based on the type of buffer substance employed within a range permitting concentrating of the target biomolecules by electrophoresis or dielectrophoresis. For example, it can be set within a range of 0.5 to 1.0

MV/in. For the above-stated reasons, the power source employed is desirably a high-frequency alternating current power source.

As set forth above, the conductivity of at least one buffer substance selected from the group consisting of phenylalanine, histidine, carnosine and arginine employed in the method of making interaction between biomolecules of the present invention is preferably from 10 to 500 $\mu\Omega^{-1}$/m, more preferably 10 to 100 $\mu\Omega^{-1}$/m. The concentration of the buffer substance is desirably suitably selected to yield a conductivity falling within the above-stated range.

EXAMPLES

The present invention will be further described below through Examples.

Example 1

Figure 8:
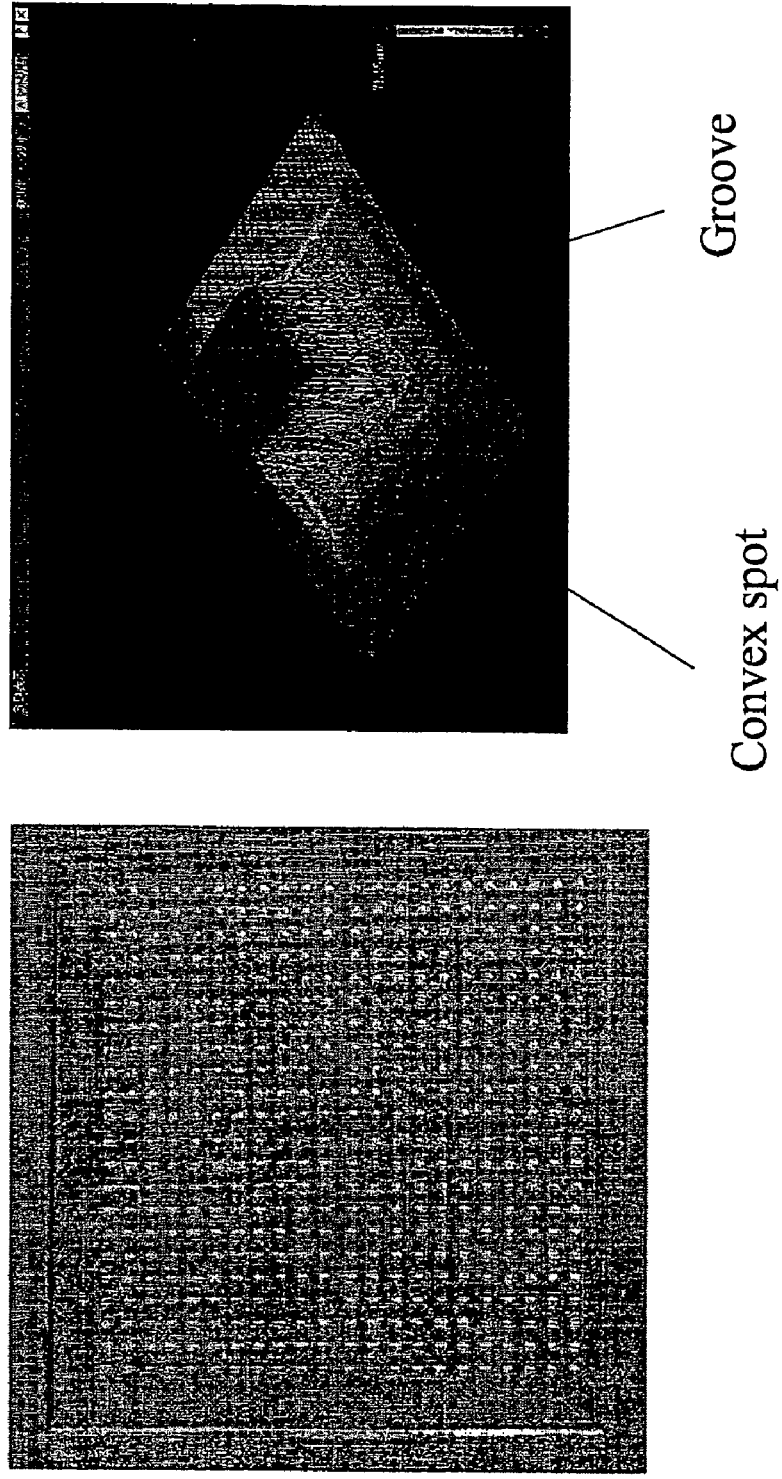
FIG. 8a) shows a digital camera image of the substrate prepared in Example 1.
Fig. 8b )shows a confocal microscopic image of the substrate prepared in Example 1.

Preparation of a substrate for nucleic acid microarray
1) After vapor-depositing chromium to a thickness of 250 Å on the surface of a surface-polished glass slide with a vacuum vapor deposition device, gold was vapor-deposited thereover to a thickness of 2,500 Å.
2) S1813 positive resist (Shipley Company L.L.C.) was applied by spin coating onto the gold-deposited glass slide and baked for one hour at 60° C. in an oven.
3) The glass slide was irradiated with ultraviolet radiation through a photomask with a UV exposure device. The photomasks employed comprised 11×11 patterns respectively of circles 200 µm in diameter and squares measuring 200 µm on a side. Following irradiation, the patterns were developed with CD-26 developing solution (Shipley Company L.L.C.) to form resist patterns of squares and circles about 200 µm in diameter on the gold surface.
4) The gold of the gold surface exposed at the perimeter of the round and square resist patterns was etched with a gold etchant (potassium iodide: iodine: water=6:1:80). Following washing with ultrapure water, chromium that had been exposed by etching the gold was etched with a chromium etchant (10 percent diceriumammonium nitrate (IV)). The substrate was then washed with ultrapure water.
5) After application of acetone to dissolve the resist, the substrate was washed with ultrapure water. To completely remove the remaining resist, piranha solution (sulfuric acid:hydrogen peroxide=1:1) was applied for 10 minutes and the substrate was washed with ultrapure water. At this stage, glass substrates having round and square patterns corresponding to the photomask were obtained.
6) Next, the above gold-patterned glass substrates were immersed for 50 minutes in 4.6 percent hydrofluoric acid to etch the exposed glass surface. This corroded the glass surface to a depth of about 50 µm. Undercutting also corroded the area under the gold pattern in a horizontal direction; the patterns of circles about 200 µm in diameter and squares about 200 µm on a side became patterns of about 90 µm (diameter or side).
7) After etching gold and chromium in the same manner as in 4), the substrates were cleaned with piranha solution and ultrapure water.
8) Chromium and gold were vapor deposited in the same manner as in 1) to prepare substrates for nucleic acid microarray with gold vapor-deposited surfaces (FIG. 8).

FIG. 8a) is a digital photograph of the substrate prepared in Example 1. The image shows the convexoconcave shape. FIG. 8b) is a photograph of an optical section taken by confocal microscopy of a square spot showing its three-dimensional structure. The formation on the substrate of protruding spot parts having flat surfaces for spotting on the top thereof can be seen. The square spots were about 50 µm in height. The flat surfaces for spotting on the substrate obtained in Example 1 were 90 µm in size, and the angle formed between the substrate surface around the protruding spot parts and the lateral surface of the protruding spot parts was 110°.

Example 2

DNA Stamping on a Substrate for Nucleic Acid Microarray

Figure 9:
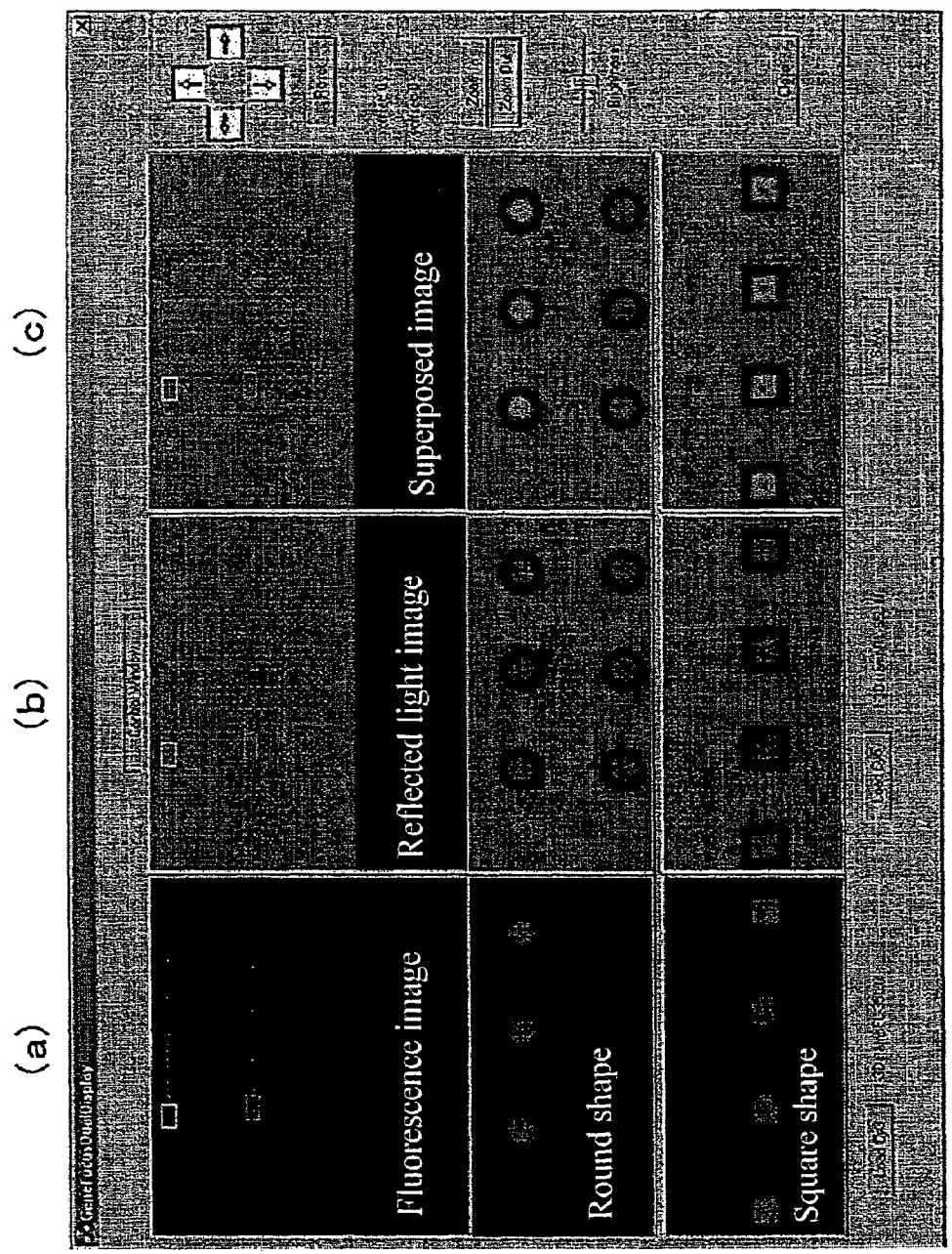
FIG. 9 shows a fluorescent image (a), reflected image (b), and superposed image of the fluorescent image and the reflected image (c) obtained in Example 2.

A solution of DNA labeled with 5'-fluorochrome Cy3 was stamped with a DNA arrayer developed by RIKEN on the flat surfaces for spotting on the top of the protruding spot parts of the substrate for nucleic acid microarray prepared in Example 1. The tip of the stamping needle was round and had a diameter of 130 µm. Using the DNA microarray scanner capable of simultaneously measuring fluorescence and reflected light shown in FIG. 7, the fluorescence and reflected light from the substrate that had been stamped with the DNA solution were measured (FIG. 9). FIG. 9(a) is a fluorescent image, (b) is a reflected light image, and (c) shows a superposed image of both images. The DNA microarray scanner employed here displays fluorescent images in red and reflected light images in green. For the round spots, round fluorescent images displayed in red are visible, and for the square spots, square fluorescent images displayed in red are visible. When these fluorescent images were superposed on reflected light images displayed in green, the shape matched the fluorescent images. Thus, the DNA stamping solution was demonstrated to have been stamped only on the flat surfaces for spotting on the top of the protruding stop parts on the substrate. In this manner, with the substrate of the present invention, it was possible to use the reflected image to confirm the size and position of the flat surfaces for spotting on the top of the protruding spot parts on the substrate and specify the areas in which DNA had been stamped.

Since the reflection focal depth of the scanner employed in the present Example was 500 µm, light reflected from the substrate surface around the protruding spot parts (difference in height with the flat surface for spotting on the top of the protruding spot parts: 50 µm) was also detected at about the same intensity as light reflected from the flat surfaces for spotting. However, since the angle formed between the substrate surface around the protruding spot parts and the lateral surface of the protruding spot parts in the present Example was 110°, portions corresponding to the lateral surface parts appeared as a black fringe in the reflected image, permitting specification of the position and size of the spots.

Example 3

Verification of the Hybridization Promoting Effect by Electrophoresis (Direct Current Load)

Thiolated DNA probe (tatgacaatg aatacggcta cagcaacagg gtggtggacc tcatg (Seq. ID No. 2), gene name: GAPDH) was immobilized on the flat surfaces for spotting on the top of the protruding spot parts on the substrate for nucleic acid microarray obtained in Example 1, and hybridization was conducted with fluorescently labeled murine cerebral cRNA.

The DNA microarray and an ITO electrode were placed so as to face each other, a sheet of 0.17 mm-thickness glass was inserted between the two for insulation, and the substrate and electrode were secured with a clip. Into the 0.17 mm gap was inserted a hybridization solution containing the above-described target (cRNA:1.45 μg (corresponding to 0.05 μg of mRNA) and hybridization buffer: 50 mM histidine). A positive electrode was connected to the DNA microarray side, and a negative electrode to the ITO electrode side. A 3V direct current load was applied for two minutes at room temperature. Subsequently, washing was conducted with 2×SSC+ 0.1% SDS, 1×SSC (150 mM sodium chloride, 15 mM sodium citrate), and 0.1×SSC.

Figure 10:
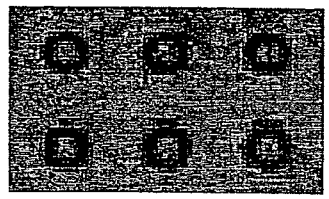
FIG. 10 a) shows a reflected image obtained in Example 3.
Figure 10:
Figure 10:

The microarray was observed with the DNA microarray scanner capable of simultaneously measuring fluorescence and reflected light shown in FIG. 7. As shown in FIG. 10, the results revealed that when a load was applied (c), a significantly stronger fluorescent signal was obtained than when no load was applied (b), clearly indicating that hybridization had been promoted by electrophoresis. When the fluorescent image was superposed on the reflected light image (a), it was possible to specify which spots had undergone hybridization.

Example 4

Verification of the Hybridization Promoting Effect by Dielectrophoresis (Alternating Current Load)

Figure 11:
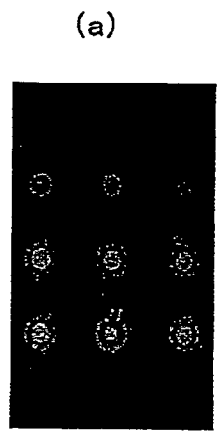
FIG. 11a) shows a reflected image obtained in Example 4.
FIGS.11b) and 11c) show fluorescent images obtained in Example 4.
Figure 11:
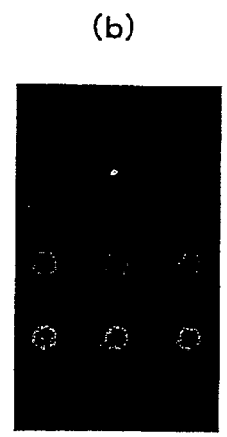
Figure 11:
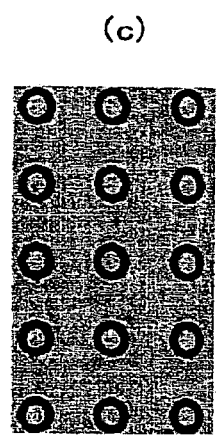
Figure 12:
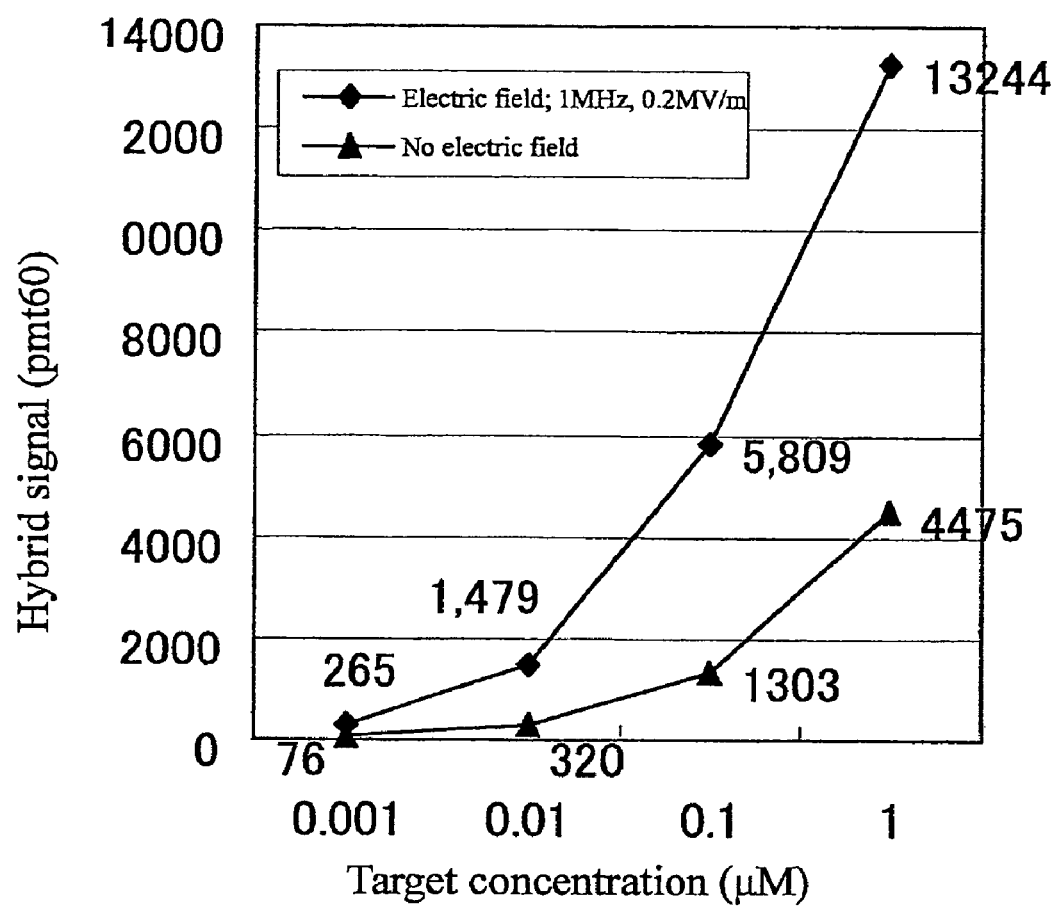
FIG. 12 is a graph showing the correlation between target concentration and fluorescent intensity in Example 4.

Five types of DNA probe (Seq. ID No. 3: ggccgttctgcttacagtggcttgcagagcagctcctacttgatg●gene name: NFL, Seq. ID No. 4: gtaccaacattgcctcctagcagagaagtgtgtgtgtgagaagcc●gene name:Ubiquitin2e, Seq. ID No. 5: ttttgtcccccaacttgatgtatgaaggctttggtctccctggg●gene name: β-actin, Seq. ID No. 6: gcagtggcaaagtggagattgttgccatcaacgaccccttcattg●gene name:gapdh, Seq. ID No. 7: agccaggaaatttgtcgagagcgcagccacttctttcagtgttgc●gene name: psbP) were terminally immobilized on the flat surfaces for spotting on the top of protruding spot parts on the substrate for nucleic acid microarray obtained in Example 1 and hybridization was conducted with a target in the form of various 5' fluorescent Cy3-labeled complementary oligo DNA. The hybridization solution was prepared using 50 mM histidine to adjust the final target concentration of the various complementary strand oligo DNA as follows: 0.001 μM for the DNA probe of Seq. ID No. 3, 0.01 μM for the DNA probe of Seq. ID No. 4, 0.1 μM for the DNA probe of Seq. ID No. 5, 1 μM for the DNA probe of Seq. ID No. 6, and 0 μM (none added) for the DNA probe of Seq. ID No. 7. The microarray was positioned so as to face a gold opposite electrode, a 0.03 mm rubber sheet was inserted for insulation between them, and the microarray and electrode were secured with a clip. A hybridization solution containing the above-described target was inserted into the 0.03 mm space, the microarray and gold opposite electrode were connected to a power source and an oscillator, and a 1 MHz, 0.2 MV/m alternating current load was applied for two minutes. The microarray was observed with the DNA microarray scanner capable of simultaneously measuring fluorescence and reflected light shown in FIG. 7. As shown in FIG. 11, the results indicated that when a load was applied (a), a clearly stronger fluorescent signal was obtained than when no load was applied (b). FIG. 12 shows the correlation between target concentration and fluorescent intensity. FIGS. 11 and 12 indicate that the promoting effect on hybridization by dielectrophoresis can be obtained by the application of an alternating current load between the microarray and the gold opposite electrode. In the present Example, the fact that the fluorescent signal obtained was dependent on the concentration of the target and the fact that no signal was detected in a negative control revealed that the degree of hybridization could be measured based on the fluorescent intensity. When the fluorescent image of FIG. 11(a) was superposed on the reflected light image of FIG. 11(c), it was possible to specify the spots that had undergone hybridization.

Example 5

The effect of Buffer on Hybridization by Dielectrophoresis

Figure 6:
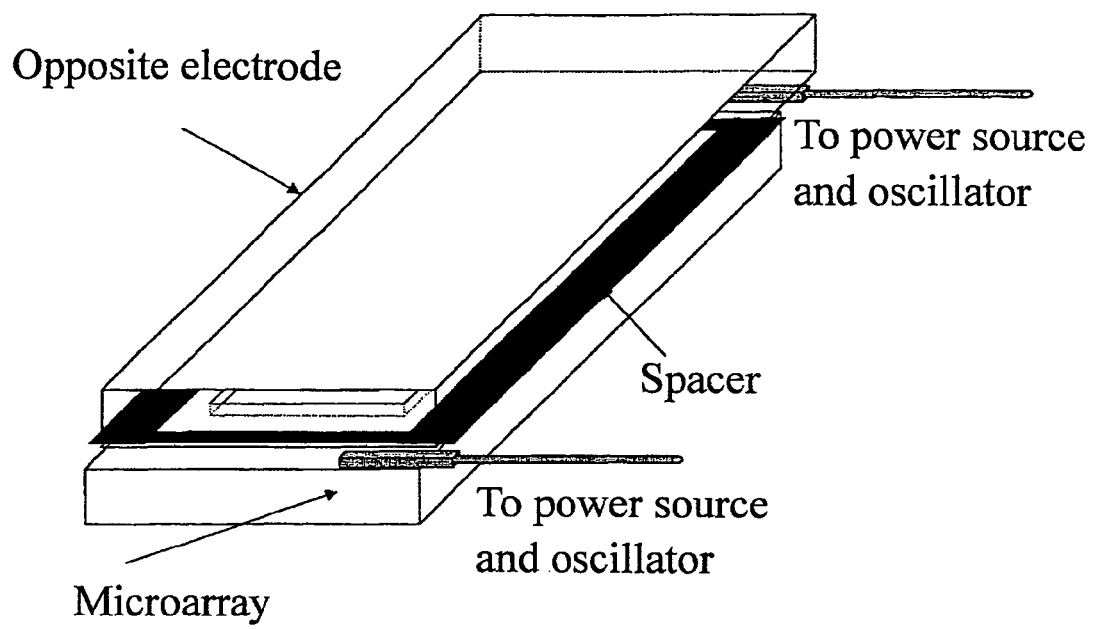
FIG. 6 shows a schematic view of the device of promoting interaction between biomolecules of the present invention.
Figure 6:
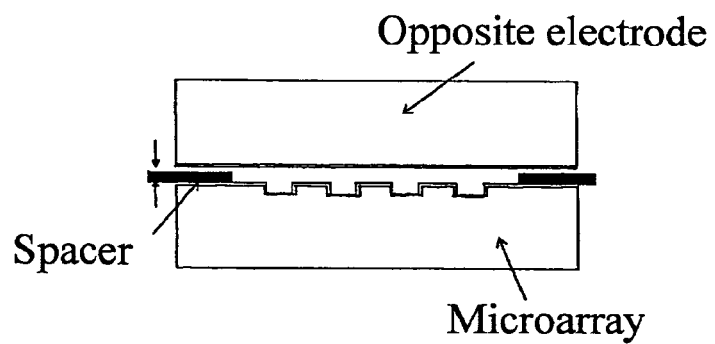
Figure 13:
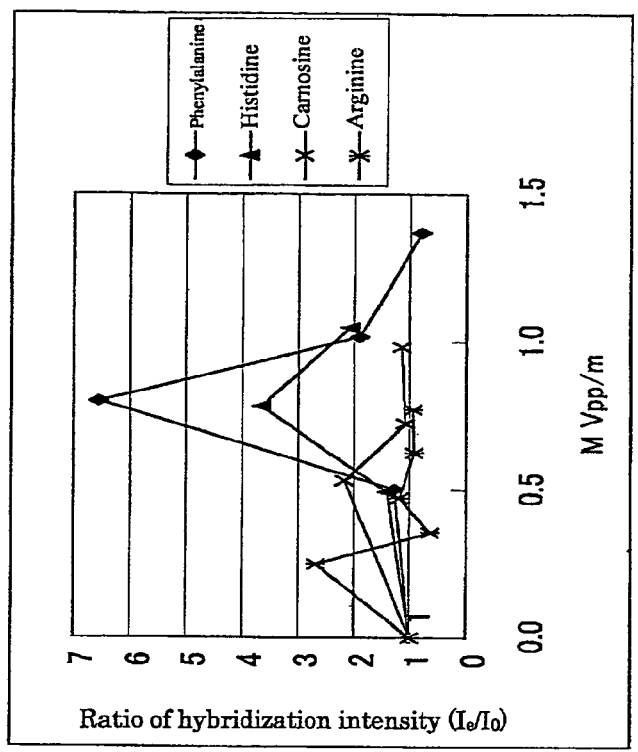
FIG. 13 is a graph showing the intensity of the hybridization signal obtained in Example 5.
Figure 13:
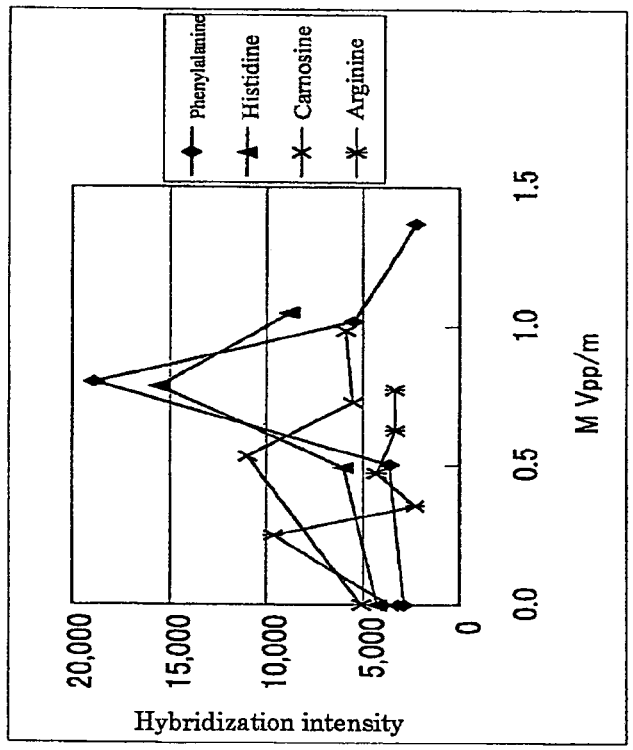

A probe DNA solution (1×microspotting solution (Terechem Corp.), 0.1 percent Tween20) was stamped to a concentration of 180 μM with the high-density arrayer on a substrate prepared in Example 1. The stamped probe gene was GAPDH (5'-gcagtggcaa agtggagatt gttgccatca acgaccccctt cattg-3'(Seq. ID No. 8)) that had been modified on the 5' end with array-use linker (Nisshinbo Industries, Inc.). Following stamping, the substrate was irradiated with 600 mJ/cm$^2$ of UV, washed twice for 5 minutes with ultrapure water, and dried. After preparing target DNA solutions (1 μM 5' terminal Cy3 fluorescent oligo DNA (a sequence complementary to the probe DNA), buffer containing 10 to 50 mM of phenylalanine, histidine, carnosine, or arginine), and the above-described array was placed on a thermal cycler set to 450° C. An insulating film 30 4μm in thickness (Teijin DuPont film) was placed along the perimeter of the array as a spacer, and 20 μL of target DNA solution were applied to the stamped area. Next, a glass slide substrate (opposite electrode) coated with an indium tin oxide (ITO) film was placed over the top and the two substrates were secured (FIG. 6). A hybridization reaction was conducted while applying an electric field of 1 MHz, 0 to 50 Vp-p for 10 minutes between the microarray and the opposite electrode. Following the reaction, the array was washed and the hybridization signal intensity was calculated. The results are given in FIG. 13. (a) is a graph showing the correlation between the electric field applied and hybridization signal intensity, and (b) is a graph of the intensity ratio (referred to hereinafter as the "rate of signal increase") to the signal obtained when hybridization was conducted without applying an electric field. Table 1 shows the results for the electric field producing the greatest rate of signal increase for each buffer. As shown in Table 1, compared to hybridization without an electric field, phenylalanine produced a hybridization increase rate of 6.54-fold with an electric field of 0.8M Vp-p/m; L-histidine, 3.66-fold with an electric field of 0.78M Vp-p/m; carnosine, 2.16-fold with an electric field of 0.53M Vp-p/m; and L-arginine, 2.66-fold with an electric field of 0.25M Vp-p/m. These results reveal that when buffers containing phenylalanine, histidine, carnosine, and arginine were employed, particularly when phenylalanine was employed, the method of promoting interaction between biomolecules of the present invention produced a good hybridization promoting effect.

TABLE 1

| Buffer | Concentration (mM) | Conductivity (μΩ⁺/M) | Electric field (MVpp/m) | Hybridization signal intensity | | Rate of signal increase (With the application of electric field/ without the application of electric field) |
| --- | --- | --- | --- | --- | --- | --- |
| | | | | With the application of electric field | Without the application of electric field | |
| DL-phenylalanine | 10 | 24 | 0.80 | 18804 | 2874 | 6.54 |
| L-histidine | 50 | 33 | 0.78 | 15557 | 4248 | 3.66 |
| Carnosine | 50 | 51 | 0.53 | 11001 | 5089 | 2.16 |
| L(+)-arginine | 50 | 61 | 0.25 | 9615 | 3612 | 2.66 |

Example 6

Effect of Promoting Hybridization by Dielectrophoresis using Real Sample cDNA

A probe DNA solution (1× microspotting solution (Terechem Corp.), 0.1 percent Tween20) was stamped to a concentration of 180 μM with a high-precision arrayer on the substrate prepared in Example 1. Table 2 gives the probe gene names and sequences of the 11 types that were stamped. Probe modified on the 5' end with array-use linker (Nisshinbo Industries, Inc.) was employed. Following stamping, the substrate was irradiated with 600 mJ/cm² of UV, washed twice for 5 minutes with ultrapure water, and dried.

A target DNA solution (5 ng/μL Cy3 murine cerebral cDNA, 50 mM L-histidine) was prepared, heated for 1 minute at 95° C., and left standing for 2 minutes at room temperature.

The DNA microarray thus obtained was placed on a thermal cycler set to 45° C., an insulating film (Teijin DuPont Film) 30 μm in thickness was positioned around the array as a spacer, and 20 μL of target DNA solution was applied to the stamp area. Next, a glass slide substrate (opposite electrode) coated with an indium tin oxide (ITO) film was placed over the top and the two substrates were sealed.

A hybridization reaction was conducted while applying an electric field of 1 MHz, 30 Vp-p for 20 minutes between the microarray and the opposite electrode. Following the reaction, the array was washed with 2×SSC/0.1% SDS, 1×SSC, 0.2×SSC solution, 5 minutes each time, at room temperature. Next, a fluorescent scanner (Gene Scope II, made by Gene Focus) was employed to calculate the intensity of the hybridization signal. The intensity ratio of the signal obtained when no electric field was applied to the signal obtained when an electric field was applied is given for each sequence in the upper portion of FIG. 15. A graph in which the signal intensity when an electric field was applied is plotted on the Y axis and the signal intensity when no electric field was applied is plotted on the X axis for each sequence is shown in the bottom portion of FIG. 15.

Figure 15:
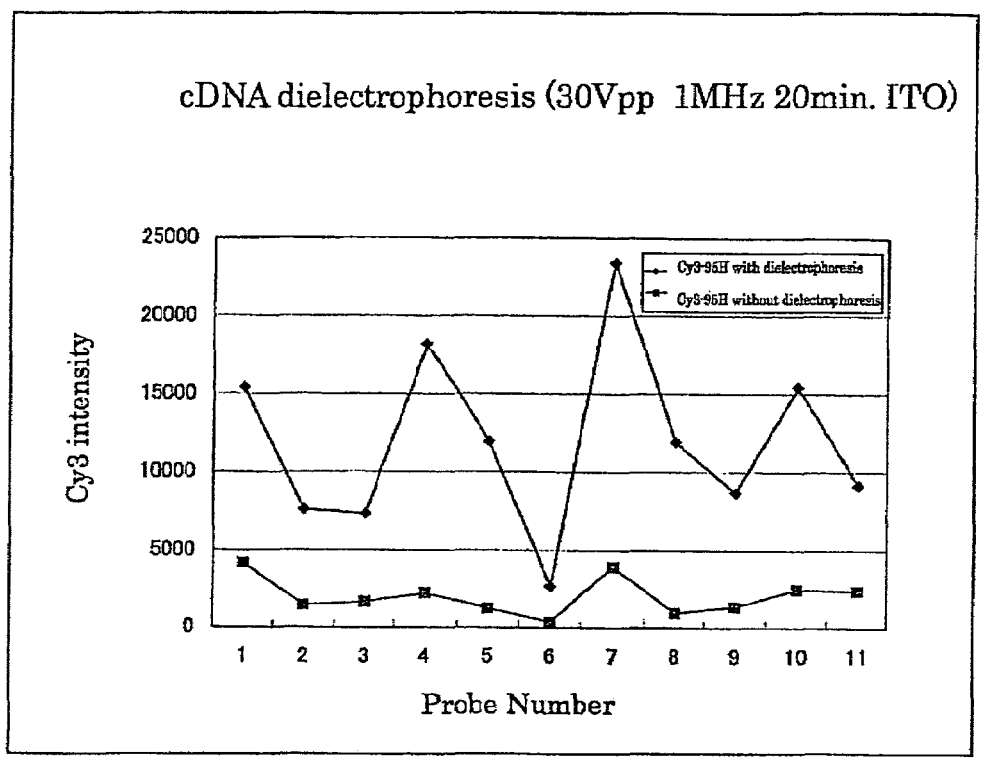
FIG. 15 is a graph comparing a hybridization signal obtained when an electric field was applied and a hybridization signal obtained when no electric field was applied in Example 6.
Figure 15:
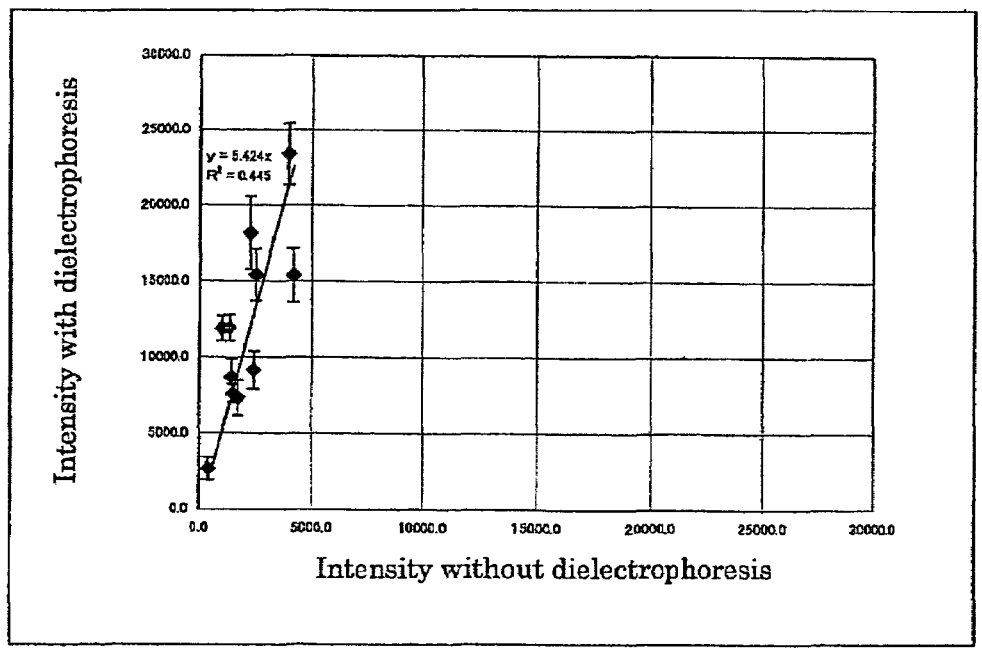

As shown in FIG. 15, relative to when no electric field was applied, there was a five-fold increase in fluorescent signal intensity for each of the sequences when an electric field was applied (FIG. 15).

TABLE 2

| (1) | beta-actin | 5'-TTTTGTCCCCCAACTTGATGTATGAAGGCTTTGGTCTCCCTGGG-3' | (Seq. ID No. 9) |
| --- | --- | --- | --- |
| (2) | NF-L | 5'-GGCCGTTCTGCTTACAGTGGCTTGCAGAGCAGCTCCTACTTGATG-3' | (Seq. ID No. 10) |
| (3) | Ubiquitin 2e | 5'-GTACCAACATTGCCTCCTAGCAGAGAAGTGTGTGTGAGAAGCC-3' | (Seq. ID No. 11) |
| (4) | hsc70 | 5'-CCTATGGTGCAGCTGTCCAGGCAGCCATTCTATCTGGAGACAAGT-3' | (Seq. ID No. 12) |
| (5) | rpL3 | 5'-GGTGAGGTGACCAATGACTTCATCATGCTCAAAGGCTGTGTGGTG-3' | (Seq. ID No. 13) |
| (6) | Akt | 5'-GCTGGACAAGGACGGGCACATCAAGATAACGGACTTCGGGCTGTG-3' | (Seq. ID No. 14) |
| (7) | Transthyretin | 5'-ACCATCGCAGCCCTGCTCAGCCCATACTCCTACAGCACCACGGCT-3' | (Seq. ID No. 15) |
| (8) | rpS5 | 5'-CATTGCTGTGAAGGAGAAGTATGCCAAGTACCTGCCCCACAGTGC-3' | (Seq. ID No. 16) |
| (9) | HCN1 | 5'-GTGCCACAGCGTGTCACCTTGTTCAGACAGATGTCCTCGGGAGCC-3' | (Seq. ID No. 17) |
| (10) | GAPDH | 5'-GCAGTGGCAAAGTGGAGATTGTTGCCATCAACGACCCCTTCATTG-3' | (Seq. ID No. 8) |
| (11) | Lhb1B2 | 5'-ACTCAAGTTATCCTCATGGGAGCTGTTGAAGGCTACAGAGTCGCC-3' | (Seq. ID No. 18) |

INDUSTRIAL APPLICABILITY

The present invention provides a substrate having biomolecule immobilization regions of prescribed shape on a biomolecule microarray, and means by which the interaction of biomolecules, particularly the hybridization of nucleic acids, is rapidly conducted, the interaction of trace quantities of sample is promoted, and the interaction is detected and analyzed rapidly and with high sensitivity.

The invention claimed is:

1. A substrate for biomolecule microarray comprising one or more spots for immobilizing a biomolecule, in which said spot for immobilizing a biomolecule protrudes from the surface of the substrate and has a flat surface for spotting on the top thereof and comprises said flat surface for spotting surrounded by a lateral surface that is inclined to said flat surface for spotting at an angle ⊖, which spot is hereinafter referred to as a "protruding spot part"; and at least the surface of the substrate around the protruding spot part and the protruding spot part, including the flat surface for spotting and the lateral surface, are comprised of an electrically conductive substance, wherein said surface of the substrate around the protruding spot part forms a roughly V-shaped bottom surface and wherein the intensity of light detected from said V-shaped bottom surface when read by a confocal detector is different from the intensity of light detected from said flat surface.

2. The substrate according to claim 1, wherein said electrically conductive substance is gold, nickel, platinum, silver, titanium, aluminum, stainless steel, copper, electrically conductive oxide, or electrically conductive plastic.

3. The substrate according to claim 1, wherein the entire substrate is comprised of an electrically conductive substance, or the substrate has a coated layer of an electrically conductive substance on the surface thereof.

4. The substrate according to claim 3 wherein the substrate having a coated layer of an electrically conductive substance is comprised of glass, metal, silicon or plastic.

5. The substrate according to claim 1, wherein said protruding spot part has a height ranging from 10 to 500 µm.

6. The substrate according to claim 1, wherein the angle formed between the flat surface for spotting on the top of said protruding spot part and the lateral surface of said protruding spot part is equal to or greater than 90°.

7. The substrate according to claim 1, wherein said flat surface for spotting is a roughened surface.

8. A biomolecule microarray comprising the substrate according to any one of claims 1 and 2-7 and at least one biomolecule; in which the biomolecule is immobilized on at least the flat surface for spotting on said substrate.

9. The biomolecule microarray according to claim 8 wherein said biomolecule is at least one selected from the group consisting of DNA, RNA, PNA, protein, polypeptide, sugar compound, lipid, natural small molecule, and synthetic small molecules.

10. A device of promoting interaction between biomolecules comprising:
    a biomolecule microarray comprising a substrate having one or more spots for immobilizing biomolecules protruding from the surface of the substrate and having a flat surface for spotting on the top thereof, which spots are hereinafter referred to as "protruding spot parts", at least said protruding spot part having a surface of an electrically conductive substance, and a biomolecule being immobilized on the surface of the electrically conductive substance of the flat surface for spotting; wherein said surface of the substrate around said protruding spot part forms a roughly V-shaped bottom surface and wherein the intensity of light detected from said V-shaped bottom surface when read by a confocal detector is different from the intensity of light detected from said flat surface;
    an electrode provided so as to face the surface having the biomolecule-immobilized spots of said microarray; and
    a power source for applying an electric field between said microarray and said electrode;
    said substrate has a terminal capable of passing an electric current to said surface of an electrically conductive substance of said protruding spot parts on the surface of said substrate in areas other than the protruding spot parts.

11. The device according to claim 10 wherein the surface of said substrate in areas other than the protruding spot parts has a coated layer of an electrically conductive substance, said terminal is comprised in said coated layer of an electrically conductive substance or capable of passing an electric current to said coated layer of an electrically conductive substance, and the coated layer of an electrically conductive substance and the surface of an electrically conductive substance of the protruding spot part are provided as an integrated coated layer of an electrically conductive substance.

12. The device according to claim 10 wherein said biomolecule is at least one selected from the group consisting of DNA, RNA, PNA, proteins, polypeptides, sugar compounds, lipids, natural small molecules, and synthetic small molecules.

13. The device according to claim 10, wherein the distance between said flat surface for spotting and the electrode ranges from 1 to 500 µm.

14. The device according to claim 10, which comprises a nonelectrically conductive spacer between said microarray and the electrode.

15. The device according to claim 10, wherein said electrode provided so as to face the surface having the biomolecule spots of the microarray is a transparent electrode.

16. The device according to claim 10, which further comprises a temperature control means.

17. A method of promoting interaction between biomolecules comprising:
    placing a solution comprising a target biomolecule between said microarray and said electrode in a device according to claim 10, and
    applying an electric field between said microarray and said electrode.

18. The method according to claim 17, wherein said electric field applied between said microarray and said electrode ranges from 0.001 to 10 MV/m.

19. The method according to claim 17 wherein said target biomolecule is labeled with a fluorophore.

20. The method according to claim 17, wherein said solution comprising a target biomolecule comprises at least one buffer substance selected from the group consisting of phenylalanine, histidine, carnosine and arginine.

21. A method of detecting interaction between biomolecules, comprising detecting using a confocal detector the interaction between a target biomolecule and a biomolecule on each biomolecule-immobilized spot of the microarray according to claim 8, that either lies in an environment permitting interaction of the immobilized biomolecule with the target biomolecule, or has previously lain in an environment permitting interaction of the immobilized biomolecule with the target biomolecule.

22. The method according to claim 21, wherein both of said biomolecule on the biomolecule-immobilized spot and said target biomolecule are labeled with a fluorophore.

23. The method according to claim 21, wherein, with said confocal detector, said protruding spot parts on the microarray are detected as a reflected image from the difference in intensity of reflected light based on differences in the height and/or shape of the protruding spot parts and other portions on the surface of the microarray.

24. The method of detecting according to claim 23 wherein the interaction between biomolecules is detected by detecting fluorescence from said protruding spot parts as a reflected image.

25. A substrate for biomolecule microarray comprising one or more spots for immobilizing a biomolecule, in which
    said spot for immobilizing a biomolecule protrudes from the surface of the substrate and has a flat surface for spotting that is a roughened surface on the top thereof and comprises said flat surface for spotting surrounded by a lateral surface that is inclined to said flat surface for spotting at an angle $\Theta$, which spot is hereinafter referred to as a "protruding spot part"; wherein said lateral surface forms a roughly V-shaped bottom surface and wherein the intensity of light detected from said V-shaped bottom surface when read by a confocal detected is different from the intensity of light detected from said flat surface; and
    at least the surface of the substrate around the protruding spot part and the protruding spot part, including the flat surface for spotting and the lateral surface, are comprised of an electrically conductive substance.

* * * * *